US012667652B2

(12) United States Patent
Friederichs et al.

(10) Patent No.: US 12,667,652 B2
(45) Date of Patent: Jun. 30, 2026

(54) MEDICAMENT PREPARATION DEVICES, METHODS, AND SYSTEMS

(71) Applicant: NxStage Medical, Inc., Lawrence, MA (US)

(72) Inventors: Goetz Friederichs, Waltham, MA (US); Gregory Yantz, Waltham, MA (US)

(73) Assignee: NxStage Medical, Inc., Lawrence, MA (US)

( * ) Notice: Subject to any disclaimer, the term of this patent is extended or adjusted under 35 U.S.C. 154(b) by 1008 days.

(21) Appl. No.: 17/708,923

(22) Filed: Mar. 30, 2022

(65) Prior Publication Data

US 2022/0313884 A1     Oct. 6, 2022

Related U.S. Application Data

(60) Provisional application No. 63/168,680, filed on Mar. 31, 2021.

(51) Int. Cl.
*A61M 1/28* (2006.01)
*A61M 1/14* (2006.01)
(Continued)

(52) U.S. Cl.
CPC .............. *A61M 1/287* (2013.01); *A61M 1/15* (2022.05); *A61M 1/1562* (2022.05);
(Continued)

(58) Field of Classification Search
CPC .. A61M 1/1656; A61M 1/159; A61M 1/1672; A61M 1/287; A61M 1/1668;
(Continued)

(56) References Cited

U.S. PATENT DOCUMENTS 4,136,708 A * 1/1979 Cosentino ........... A61M 1/1656
222/64
4,892,706 A * 1/1990 Kralovic .................. A61L 2/18
204/196.15
(Continued)

FOREIGN PATENT DOCUMENTS

EP        1312386 A2      5/2003
JP     2009533092 A       9/2009
(Continued)

OTHER PUBLICATIONS

Mizzi, L et al. "Assessing the individual microbial inhibitory capacity of different sugars against pathogens commonly found in food systems." Letters in applied microbiology vol. 71,3 (2020): 251-258. doi: 10.1111/lam.13306 (Year: 2020).*
(Continued)

*Primary Examiner* — Jason E Flick
*Assistant Examiner* — Isabella S North
(74) *Attorney, Agent, or Firm* — Potomac Law Group, PLLC

(57) ABSTRACT

A system for preparing a medicament for use by a medicament user includes a proportioning machine with a controller and pumping and clamping actuators to engage a fluid circuit having pumping and clamping portions that engage with respective actuators of the proportioning machine. The fluid circuit includes a mixing container that is initially empty and later filled with two different concentrated medicaments from different concentrate containers and with purified water. The proportioning machine is configured to receive purified water and to mix it with the concentrated medicaments to produce a medicament and to output the medicament to a medicament consumer in such a way that to the medicament consumer the medicament appears to be provided from a bag of medicament. Custom mini batches of
(Continued)

medicament may be produced by varying the amount of the concentrates and water.

15 Claims, 15 Drawing Sheets

(51) Int. Cl.

| | |
|---|---|
| *A61M 1/16* | (2006.01) |
| *A61M 39/28* | (2006.01) |
| *H01M 50/119* | (2021.01) |
| *H01M 50/121* | (2021.01) |
| *H01M 50/122* | (2021.01) |
| *H01M 50/131* | (2021.01) |

(52) U.S. Cl.
CPC ........ *A61M 1/1656* (2013.01); *A61M 1/1672* (2014.02); *A61M 39/281* (2013.01); *H01M 50/119* (2021.01); *H01M 50/121* (2021.01); *H01M 50/122* (2021.01); *H01M 50/131* (2021.01); *A61M 2205/15* (2013.01); *A61M 2205/3317* (2013.01); *A61M 2205/3331* (2013.01); *A61M 2205/3368* (2013.01)

(58) Field of Classification Search
CPC .......... A61M 1/15; A61M 1/155; A61M 1/28; A61M 5/19; A61M 1/1666; A61M 1/1657
USPC .......................................................... 604/29
See application file for complete search history.

(56) References Cited

U.S. PATENT DOCUMENTS

| | | | |
|---|---|---|---|
| 5,511,875 | A | 4/1996 | Jonsson et al. |
| 5,591,344 | A | 1/1997 | Kenley et al. |
| 6,280,632 | B1 | 8/2001 | Polaschegg |
| 8,191,339 | B2 | 6/2012 | Tribble et al. |
| 9,867,929 | B2 | 1/2018 | Searle et al. |
| 11,207,454 | B2 | 12/2021 | Wyeth et al. |
| 2008/0230450 | A1 | 9/2008 | Burbank et al. |
| 2013/0168316 | A1 | 7/2013 | Noguchi et al. |
| 2015/0005699 | A1 | 1/2015 | Burbank et al. |
| 2017/0290970 | A1 | 10/2017 | Friederichs et al. |
| 2017/0319768 | A1 | 11/2017 | Szpara et al. |
| 2018/0104400 | A1 | 4/2018 | Burbank et al. |
| 2018/0326138 | A1 | 11/2018 | Kalaskar et al. |
| 2019/0151526 | A1 | 5/2019 | Wieslander et al. |
| 2019/0201607 | A1 | 7/2019 | Öberg |
| 2019/0217000 | A1 | 7/2019 | Burbank et al. |
| 2019/0262522 | A1 | 8/2019 | Wyeth et al. |
| 2019/0262524 | A1 | 8/2019 | Wyeth et al. |
| 2019/0262526 | A1* | 8/2019 | Wyeth ................ A61M 1/1664 |
| 2019/0275226 | A1 | 9/2019 | Burbank et al. |
| 2020/0009308 | A1 | 1/2020 | Friederichs et al. |
| 2020/0016317 | A1 | 1/2020 | Kelly et al. |
| 2020/0171230 | A1 | 6/2020 | Brugger et al. |
| 2020/0254167 | A1 | 8/2020 | Rohde et al. |
| 2020/0390954 | A1 | 12/2020 | Rovatti et al. |
| 2022/0126005 | A1 | 4/2022 | Friederichs et al. |

FOREIGN PATENT DOCUMENTS

| | | | |
|---|---|---|---|
| JP | 2018134444 | A | 8/2018 |
| WO | 2013141896 | A1 | 9/2013 |
| WO | 2020237033 | A1 | 11/2020 |
| WO | 2021101899 | A1 | 5/2021 |
| WO | 2022086922 | A2 | 4/2022 |
| WO | 2022204253 | A1 | 9/2022 |

OTHER PUBLICATIONS

Gotch et al., "Mechanisms determining the ratio of conductivity clearance to urea clearance," Kidney International, vol. 66, Supplement 8, Jul. 2004, pp. S-3-S-24.

International Search Report and Written Opinion mailed Aug. 1, 2022 for International Patent Application No. PCT/US2022/022591.

International Search Report and Written Opinion mailed Aug. 30, 2022 for International Patent Application No. PCT/US2022/020583.

International Search Report and Written Opinion mailed Jun. 24, 2022 for International Patent Application No. PCT/US2022/021501.

International Search Report and Written Opinion mailed Sep. 9, 2022 for International Application No. PCT/US2022/021955.

Office Action (Communication Pursuant to Article 94(3) EPC) dated Apr. 19, 2024 for European Patent Application No. 21806560.5.

Extended European Search Report dated Jul. 8, 2024 for European Patent Application No. 22772141.2.

Partial Supplementary European Search Report dated Jul. 4, 2024 for European Patent Application No. 22772033.1.

International Search Report and Written Opinion mailed Jun. 14, 2022 for International Patent Application No. PCT/US2022/021477.

International Search Report and Written Opinion mailed Jun. 3, 2022 for International Patent Application No. PCT/US2022/020331.

International Search Report and Written Opinion mailed Mar. 21, 2022 for International Patent Application No. PCT/US2021/055550.

Invitation to Pay Additional Fees mailed Apr. 29, 2022 for International Patent Application No. PCT/US2022/020583.

Invitation to Pay Additional Fees mailed Jun. 3, 2022 for International Patent Application No. PCT/US2022/022591.

Invitation to Pay Additional Fees mailed May 26, 2022 for International Patent Application No. PCT/US2022/021955.

Extended European Search Report dated Feb. 4, 2025 for European Patent Application No. 22782109.7.

Office Action (Notice of Reasons for Refusal) mailed Apr. 22, 2025 for Japanese Patent Application No. 2023-523619.

* cited by examiner

1000

1002

MEDICAMENT PREPARATION DEVICES, METHODS, AND SYSTEMS

CROSS-REFERENCE TO RELATED APPLICATIONS

This application claims the benefit of U.S. Provisional Application No. 63/168,680 filed Mar. 31, 2021, which is incorporated herein by reference in its entirety.

BACKGROUND

The disclosed subject matter relates generally to devices, methods, systems, improvements, and components for preparing medicaments and making medicament available for use by a consumer, for example, a dialysis cycler.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal dialysis fluid is infused into a patient's peritoneal cavity using a catheter that has been inserted through the abdominal wall. The fluid remains in the peritoneal cavity for a dwell period. Osmotic exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysis fluid is removed from the body cavity through the catheter.

SUMMARY

Methods, device, and systems for preparing medicaments such as, but not limited to, dialysis fluid are disclosed. In embodiments, medicament is prepared at a point of care (POC) automatically using a daily sterile disposable fluid circuit, one or more concentrates to make batches of medicament at the POC. The dialysis fluid may be used at the POC for any type of renal replacement therapy, including at least peritoneal dialysis, hemodialysis, hemofiltration, and hemodiafiltration.

In embodiments, peritoneal dialysis fluid is prepared at a point of use automatically using a daily sterile disposable fluid circuit and one or more long-term concentrate containers that are changed only after multiple days (e.g. weekly). The daily disposable may have concentrate containers that are initially empty and are filled from the long-term concentrate containers once per day at the beginning of a treatment.

Embodiments of medicament preparation, devices, systems, and methods are described herein. The features, in some cases, relate to automated dialysis such as peritoneal dialysis, hemodialysis and others, and in particular to systems, methods, and devices that prepare peritoneal dialysis fluid in a safe and automated way at a point of care. The disclosed features may be applied to any kind of medicament system and are not limited to dialysis fluid.

In embodiments, a system that prepares a medical fluid is configured in such a manner that it outputs the medical fluid to a consuming process (for example, a peritoneal dialysis cycler) wherein the consuming process does not distinguish between the system that prepares the medical fluid and pre-packaged bags of dialysate. This allows embodiments of the presently disclosed system for preparing the medical fluid to be used with any type of a cycler, without any special customization or modification of the cycler.

In embodiments, a peristaltic pump operates in only a single direction when metering medicament concentrate(s) and water into a mixing container, which provides greater accuracy as compared to a situation where the pump operates in two directions. In embodiments, when medicament concentrate(s) and/or water are being metered by the peristaltic pump, the fluid circuit is configured in a way that avoids negative upstream pressure for the pump, which further increases metering accuracy. Negative upstream pressure may be caused by filers in the fluid path upstream of the pump. In embodiments, a concentrated medicament is pumped into various portions of a fluid circuit to inhibit bacterial growth in those portions of the fluid circuit. In embodiments, the concentrated medicament is pumped into a drain line to inhibit bacterial growth in the drain line.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
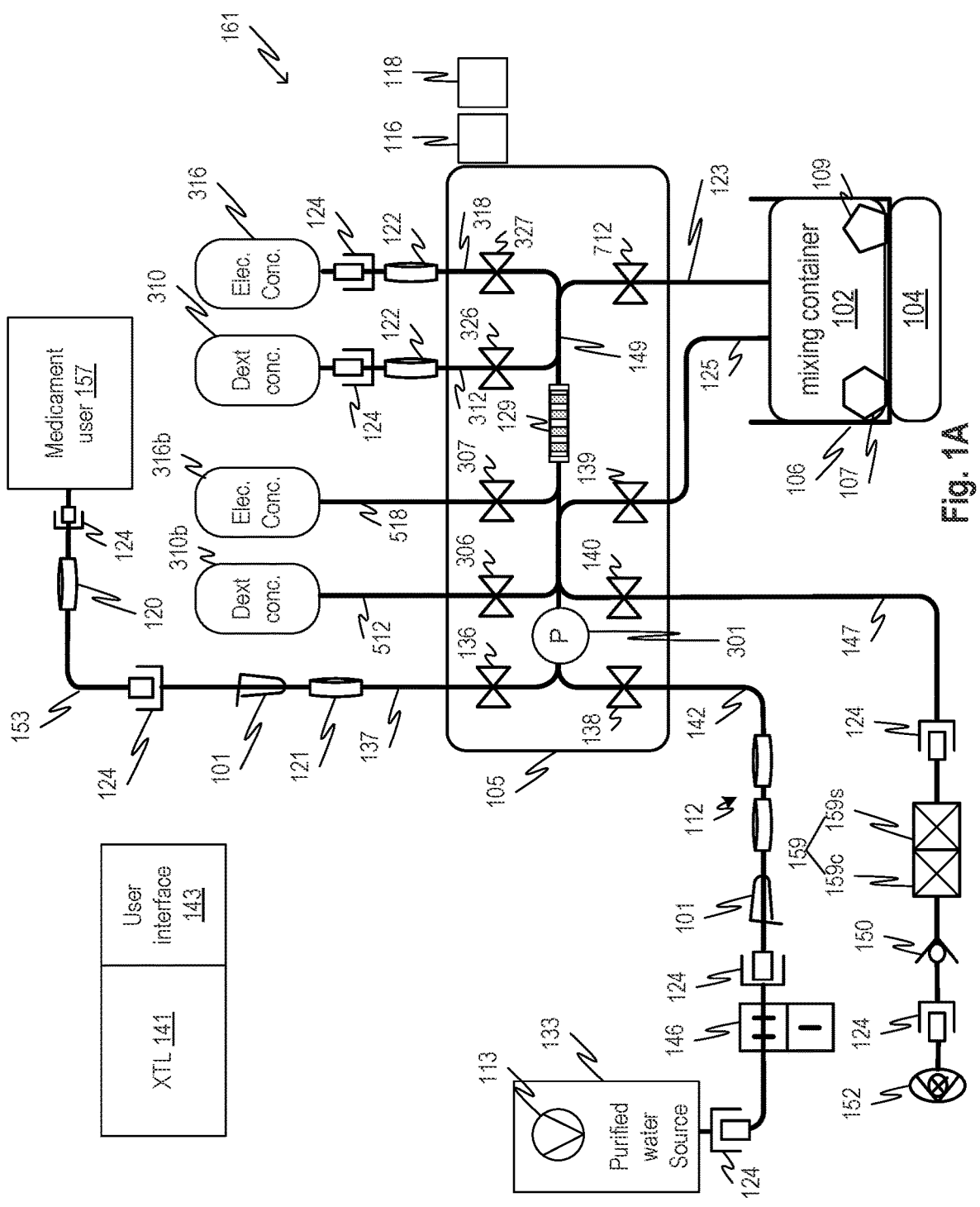
FIG. 1A shows a system for preparing a ready-to-use medicament from concentrated medicament and water according to embodiments of the disclosed subject matter.

FIG. 1A shows an embodiment of a system that uses water and up to two concentrated medicaments (also referred to as "medicament concentrates" or "concentrates") in containers 310 and 316 to make a therapeutic fluid that can be used for treatment according to embodiments of the disclosed subject matter. In embodiments, the concentrated medicament in container 310 is an osmotic agent. In embodiments, the osmotic agent includes concentrated dextrose solution. In other embodiments, the osmotic agent includes concentrated glucose solution. In embodiments, the concentrated medicament in container 316 is an electrolyte concentrate.

The system illustrated in FIG. 1A has a multi-day osmotic agent concentrate 310 which is connected to supply line 312 via a connector 124 to a disposable component 161 (described further below). In embodiments, the multi-day osmotic agent concentrate 310 contains a dextrose concentrate. In other embodiments, the multi-day osmotic agent concentrate 310 contains a glucose concentrate. A sterilizing filter (such as a 0.2 micron filter) 122 is connected inline along supply line 312, between the connector 124 and the rest of the disposable component 161, to reduce the possibility of non-sterile materials entering the fluid circuit that forms a part of the disposable component 161. Any fluid from the osmotic agent concentrate container 310 will pass through the filter 122 and pathogens will be removed or reduced by the filter 122. A controllable valve 326 can open and close, and thereby permit or prevent flow through supply line 312.

A single day osmotic agent container 310b is pre-connected and forms a part of the disposable component 161 as shown in FIG. 1A. Initially, the single day osmotic agent concentrate container 310b may be empty at the time when the disposable component 161 is connected to the system. As described below with reference to FIG. 4C, medicament concentrate from the multi-day osmotic agent concentrate container 310 is conveyed through the fluid circuit of the disposable component 161 into the single day osmotic agent concentrate container 310b at various times. In embodiments, one of the various times is when the disposable component is initially connected to the system. In other embodiments, one of the various times is when a command to generate medicament is received by a user interface of the system, such as user interface 143. Fluid flow in and out of the single day osmotic agent concentrate container 310b is permitted or prevented by controllable valve 306, which is controlled by the controller 141.

A multi-day electrolyte concentrate container 316 is also connected via its own connector 124 to supply line 318 the disposable component 161 as shown in FIG. 1A. A sterilizing filter (such as a 0.2 micron filter) 122 is connected inline along supply line 318, between the connector 124 and the rest of the disposable component 161, to reduce the possibility of non-sterile materials entering the fluid circuit that forms a part of the disposable component 161. Any fluid from the multi-day electrolyte concentrate container 316 will pass through the filter 122 and pathogens will be removed or reduced by the filter 122. A controllable valve 327 can open and close, and thereby permit or prevent flow through supply line 318.

A single day electrolyte concentrate container 316b is pre-connected and forms a part of the disposable component 161 as shown in FIG. 1A. Initially, the single day electrolyte concentrate container 316b may be empty at the time when the disposable component 161 is connected to the system. As described below with reference to FIG. 4D, medicament concentrate from the multi-day electrolyte concentrate container 316 is conveyed through the fluid circuit of the disposable component 161 into the single day electrolyte concentrate container 316b at various times. In embodiments, one of the various times is when the disposable component is initially connected to the system. In other embodiments, one of the various times is when a command to generate medicament is received by a user interface of the system, such as user interface 143. Fluid flow in and out of the single day electrolyte concentrate container 316b is permitted or prevented by controllable valve 307, which is controlled by the controller 141.

Still referring to FIG. 1A, a purified water source 133 with a water pump 113 supplies highly purified water through a connector 124 through a water line 142. The water line 142 has a non-reopenable clamp 146, another connector 124, a manual tube clamp 101, and a pair of redundant 0.2-micron sterilizing filters 112, as shown. In embodiments, different types of sterilizing filters may be used, and not limited to 0.2 micron, or to two redundant filters. For example, a single filter may be used, and a testing protocol provided to ensure that the filter does not fail before replacement.

A water inlet clamp 138, batch release clamp 136, and a conductivity sensor clamp 140 are controlled by the controller 141, which may be operatively coupled to the user interface 143, which may include a visual and/or audible output and various devices for receiving user input. The controller 141 controls the pinch clamps and a peristaltic pump 129 to make a batch of diluted concentrate in a mixing container 102 by diluting medicament concentrate (e.g., dialysis fluid concentrate) in the mixing container 102. The mixing container 102 is supplied empty and permanently connected to a fluid circuit that includes fluid lines 149, 123, and 125. A controllable valve 712 can be opened or closed to permit or prohibit flow into and out of the mixing container 102.

A pressure sensor 301 is provided in the flow path as shown and outputs a signal representative of the pressure in the fluid lines that are fluidly connected to the pressure sensor. This pressure signal may be provided to controller 141.

The mixing container 102 may be a part of a disposable component 161 that is replaced regularly, such as with each batch, every day, every week, or every month. In an embodiment, the mixing container 102 is empty initially when the disposable component 161 is connected to the system.

The mixing container 102 is fluidly connected to inlet line 123 and to inlet line 125. Inlet line 125 can be selectively closed and opened by controllable valve 139 and inlet line 123 can be selectively closed and opened by controllable valve 712. Inlet lines 123 and 125 can also be used to withdraw fluid from the mixing container 102.

The mixing container 102 may be made of a flexible material, such as a polymer so its shape is not rigid. To provide support for the mixing container 102, the mixing container 102 is held by a tub 106 which is sufficiently rigid to support the mixing container 102 when it is full of fluid. A leak sensor 107 is provided in the tub 106 and it detects leaks into the tub 106 while a temperature sensor 109 may also be provided in or on the tub 106 and it detects the temperature of the fluid in the mixing container 102. A warmer 104 may be provided as shown to provide heat to tub 106, but the warmer 104 may be omitted if another heater exists elsewhere in the system. Note that the concentrates from containers 310b and 316b that will be supplied to the mixing container 102 may be used for making any type of medicament, not just dialysis fluid.

Figure 4A:
FIGS. 4A and 4B show configurations of the systems providing water to a mixing container according to embodiments of the disclosed subject matter.
Figure 4B:
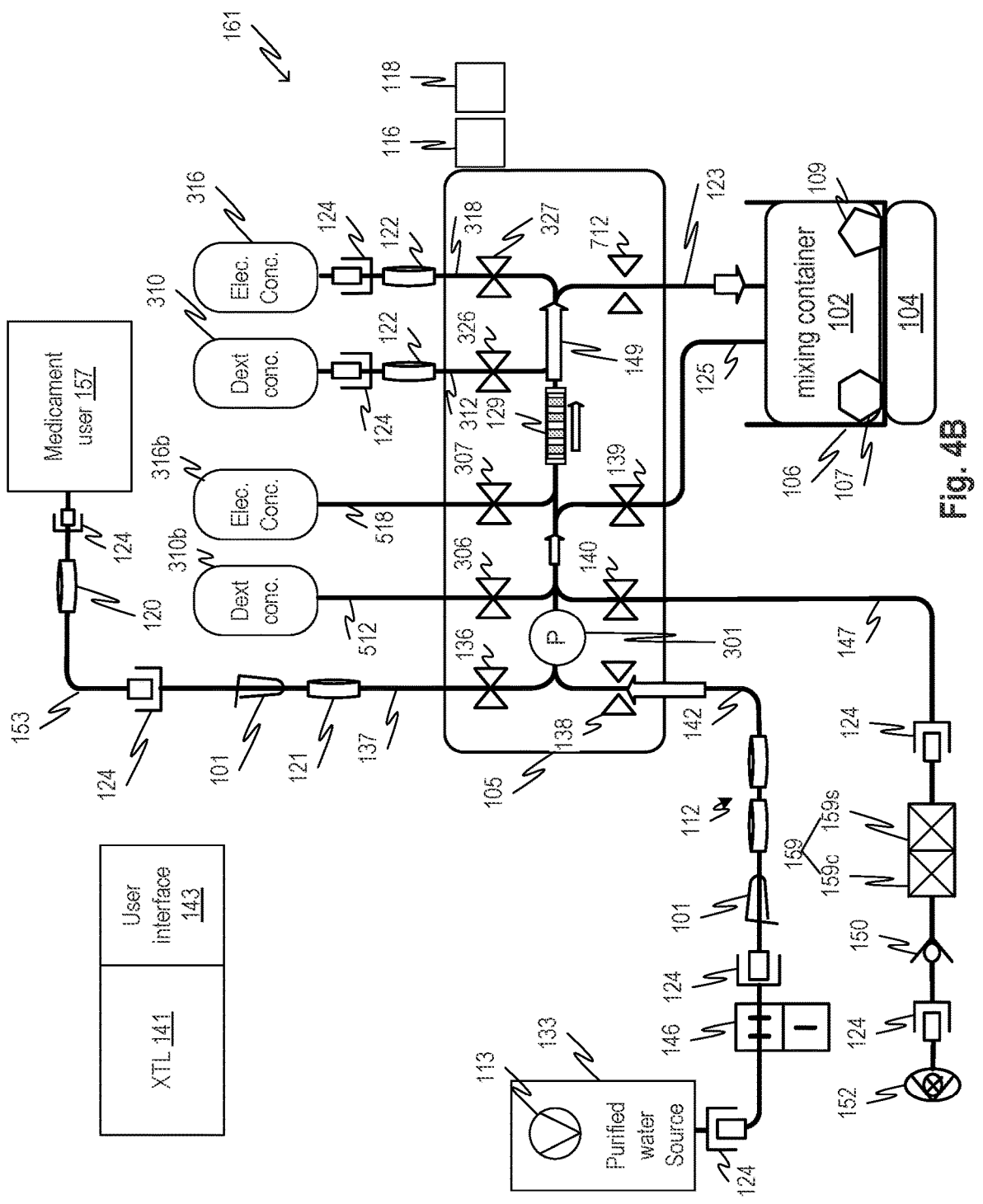

To supply water to mixing container 102, clamp 139 can remain closed, and pump 129 runs to move the water from water line 142 to inlet line 123 and mixing container 102 while valves 138 and 712 are open, as shown in FIG. 4B. The pump 113 of the purified water source 133 conveys purified water along water supply line 142 toward peristaltic pump 129. Peristaltic pump 129 thus experiences positive upstream pressure, which improves the accuracy of the metering by pump 129, so that the quantity of water that is conveyed through inlet line 123 can be precisely controlled and measured.

In embodiments, such as shown in FIG. 4A, supply line clamp 139 may be opened and the water source pump 113 operates to convey water through inlet line 125 into mixing container 102 without the use of peristaltic pump 129.

Once medicament in mixing container 102 is ready for use by the medicament user 157, clamps 136 and 139 can be opened and the other clamps may be closed, and the medicament pump 115 may draw from the mixing container 102 without the assistance of a predefined backpressure, hence without the use of peristaltic pump 129. Alternatively, the peristaltic pump 129 may be run through a circulating path of 149, 123, and 125 with a feedback-controlled clamp 139 according to pressure indicated by pressure sensor 301. Here, clamps are closed except for clamps 136 and 712, and the medicament user 157 draws from a pressurized line.

Two conductivity/temperature sensors 159c and 159s are positioned on the drain line 147, beyond connector 124, but it will be understood that a single conductivity/temperature sensor 159 may include two conductivity sensors 159c and 159s. The conductivity/temperature sensor 159 is positioned on a portion of aligned switches connectable by connector 124, such that when the disposable component 161 is replaced, the conductivity/temperature sensor 159 can remain and can be reused.

The mixing container at 102 may be part of a disposable unit 161. Included in a disposable unit 161 are two concentrate supply lines 312 and 318 with respective sterilizing filters 122 (to reduce touch contamination) and connectors 124, transfer line 149, water source line 142, drain conductivity line 147, medicament supply line 153 and the mixing container 102 with its respective fill lines 123 and 125. In addition, daily use containers 310b and 316b are included in the daily disposable unit 161. These containers are pre-connected (e.g., heat welded) to the rest of the fluid circuit that forms daily disposable unit 161 and are initially empty. During use, the containers 310b and 316b will become filled with concentrated medicament, and later drained (fully or partially) as the concentrated medicament is withdrawn from the containers 310b and 316b and supplied to the mixing container 102.

The disposable unit 161 is permanently interconnected up to and including an end of each of the connectors 124, through which various other components can be connected (including the medicament user 157, the purified water source 133, the osmotic agent concentrate 310, the electrolyte concentrate 316, and the drain connection 152). The disposable unit 161 can be connected to check valve 150 which prevents back flow in the drain conductivity line 147.

A door lock 116 is provided adjacent a user interface door 105 to lock the user interface door. A physical door 105 that opens encloses and provides access to the interior of the fluid preparation system may have a user interface on it which may be a part of user interface 143. A door sensor 118 detects whether the door lock is in an open or a locked position to ensure that all clamps and the peristaltic pump actuators are fully engaged with the disposable fluid circuit.

The door sensor 118 may include a plunger which is pressed in when the door is closed and outputs an electrical signal to indicate whether or not the door is closed. In other embodiments, the door sensor 118 may include a magnetic reed switch which detects the presence or the absence of a magnet which is located on the door 105 at a location which is detectable by the reed switch. Purified water flows into the disposable circuit where a pair of 0.2-micron filters 112 (also in the disposable unit 161) are located to ensure that any touch contamination is prevented from flowing into the disposable circuit. An optional sterilizing filter 120 may be provided in a user medicament supply line 153. The mixing container 102 of the disposable unit 161 may have sufficient volume for a single treatment or in embodiments, multiple treatments.

The medicament output line 137 may include an optional air removal filter 121. The air removal filter 121 may be a 1.2 μm filter which removes air.

A check valve 150 in drain conductivity line 147 ensures the flow does not reverse to safeguard against contamination in the medicament or water lines or other sterile fluid circuits.

Note that in variations of most of the embodiments, the purified water source 133 may include a container or containers of purified water such as one or more polymer bags. In such embodiments, there may be a water pump arranged in a "pull" configuration. In any of the embodiments, the medicament user 157 may include a pump 115 (see FIG. 8B). For example, the medicament user 157 may include a dialysis cycler that is configured to draw from a container of dialysis fluid.

To permit the medicament user 157 to draw medicament on-demand, the controller 141 may be programmed to maintain a constant pressure that is compatible with a pump, such as the pump 115, in the medicament user 157. For example, the pressure-based control using the pressure sensor 301 may maintain a pressure that mimics a simple container that allows the medicament user 157 to draw from a container of dialysis fluid.

In embodiments, the medicament user 157 can use its own pump, such as the pump 115, to move fluid from the mixing container 102 without the use of pump 129. In this example, valves 136 and 139 will be opened, and the medicament user 157 will operate its pump 115 to draw fluid form the mixing container 102. In embodiments, the mixing container 102 may be elevated vertically above the medicament user 157 such that gravity will generate a head pressure that will convey fluid from the mixing container 102 to medicament user 157 when valves 136 and 139 are opened.

Figure 2A:
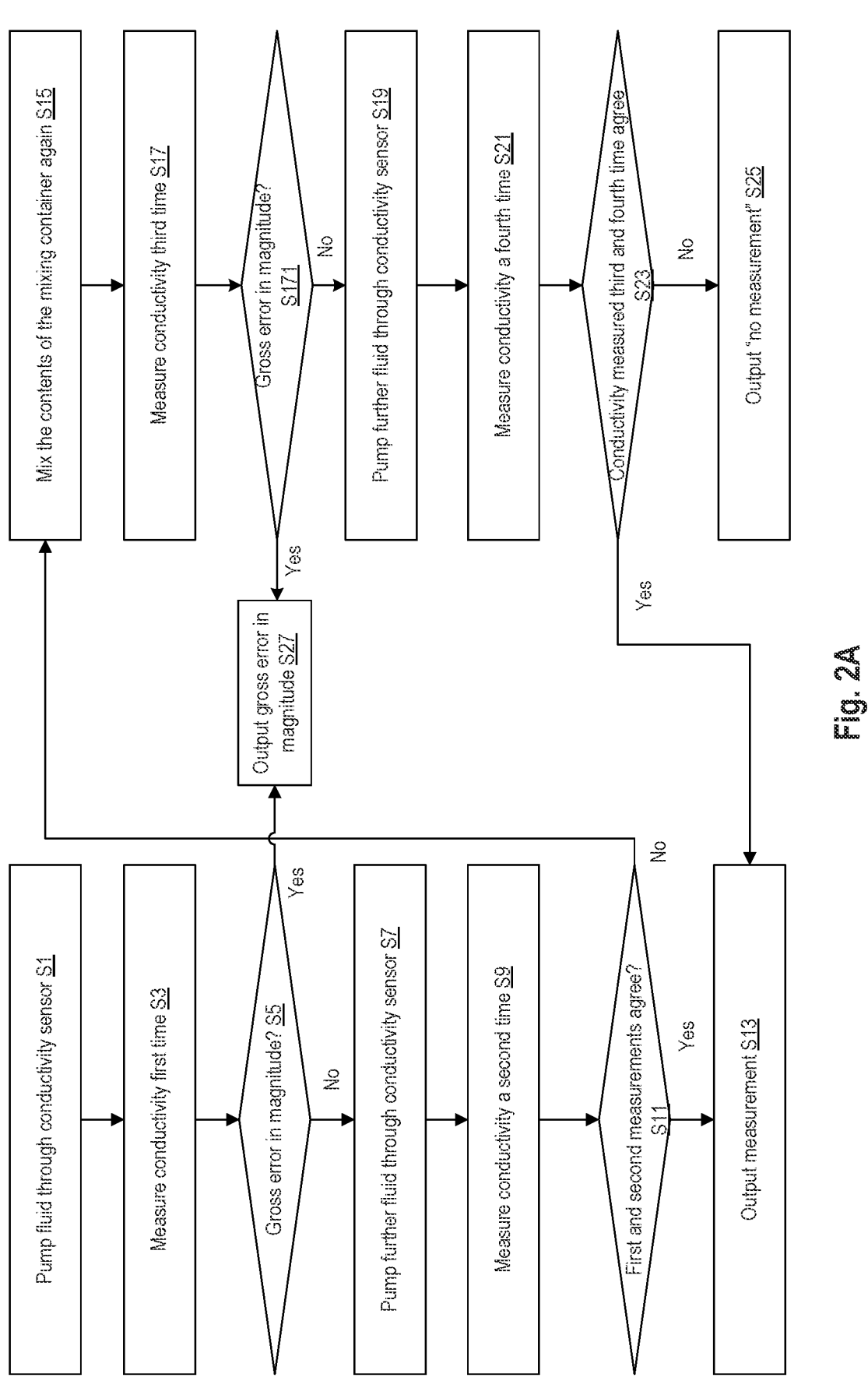
FIG. 2A shows a flow chart of a method for checking the concentration and/or conductivity of medicament according to embodiments of the disclosed subject matter.

FIG. 2A shows a procedure for reliably measuring the conductivity of a fluid. The fluid circuit will be configured as shown in FIG. 7. In this procedure two consecutive measurements are made of conductivity and temperature at different times so that the conductivity is measured for two different parts of a flow stream. The two consecutive measurements can be made with a single sensor 159 at two different times, or they may be made using two different sensors such as 159*c* and 159*s*. If the two different readings are within a predefined range of each other, the controller 141 mixes contents of the mixing container 102 a second time. The measurements are compared again and if the two conductivity are within a predefined range of each other, the measurement is output as correct. If the two measurements show a difference in concentration beyond the predefined range, then the mixing container is mixed again (configuration of FIG. 6A) and two consecutive measurements are taken again. The contents of drain line 147 may be purged to the drain. The rationale behind this is that a difference in magnitude of the consecutive measurements may be caused by inadequate mixing. If, after mixing again and repeating the two consecutive measurements, the magnitudes are still outside of the predefined range of each other, then the controller outputs a measurement failure or data indicating "no measurement." Also, after the initial measurement the controller determines if there is gross disparity between the measurement and a predefined or calculated estimate then the algorithm will immediately output an indication and stop the process.

Mixed fluid is pumped through temperature and conductivity sensors 159*c* and 159*s* and is determined to be mixed when two consecutive measurements of the conductivity of mixed fluid flowing through the temperature and conductivity sensors 159*c* and 159*s* are within a predefined range of each other. If the measurements of the conductivity differ by a margin greater than the predefined range, the mixing container 102 may be mixed again. An attachment to drain or waste container is provided by a drain connector 152.

Referring to FIG. 2A, at S1, the fluid whose conductivity is to be measured is pumped through conductivity/temperature sensors 159*c* and 159*s* by opening the conductivity sensor clamp 140 and closing the other clamps, as shown in FIG. 7. At S3, the peristaltic pump 129 is run in a direction indicated by the arrows as shown in FIG. 7. The conductivity is measured a first time by flowing mixed fluid from the mixing container 102 through the temperature and conductivity sensors 159*c* and 159*s* (or single conductivity sensor 159, depending on the configuration of the system) and storing a magnitude or multiple magnitude readings thereof. If the absolute value of the difference between the measured conductivity readings is greater than a predefined magnitude at S5, then control goes to S27 where an error indication is output. Otherwise, at S7, additional fluid is pumped from the mixing container 102 and at S9, the conductivity is measured a second time at S9. At S11 it is determined if the first and second measurements agree within a predefined range. If the measurements differ less a than predefined range, then the measurement is output at S13 where the output measurement may be one of the first and second measurements or an average of the measured values. If the measurements differ by more than the predefined range, then control proceeds to S15 where the mixing container contents are mixed again (because it is assumed that the measurements may differ due to insufficient mixing such that the medicament is not yet uniformly mixed in the mixing container 102). At S17, a third measurement for the conductivity is obtained. If the measured conductivity differs from the expected conductivity by a predefined magnitude at S171, a gross error is detected at S27. Otherwise, the process continues at S19, where the mixing container contents are again pumped through the conductivity sensors 159*c* and 159*s* and a fourth measurement of conductivity is made at S21 in the manner described above. At S23 it is determined if the third and fourth measurement are within the predefined range and if so, at S25, the measured values (average of the two sensors or one of them) are output at S13 as a valid conductivity measurement. If the measured values still disagree by the predefined amount, then at S25 a failure is output.

Note that the consecutive measurements may be done sequentially in time using one temperature-compensated conductivity measurement indicated by conductivity/temperature sensor 159*c*, only. The fluid then is conveyed, and a temperature-compensated conductivity measurement is measured again by the same sensor. In alternative embodiments, separate pairs of conductivity/temperature sensors or single conductivity/temperature sensors may be separated along a line and the measurement generated by them may be compared instead.

Note that temperature-compensated conductivity is intended to refer to a number that is proportional to concentration and may be determined in various ways including but not limited to a lookup table and a formula. For the remainder of this disclosure a reference conductivity the reference may be understood to mean temperature-compensated conductivity or an actual calculation of concentration. That is, the temperature-compensated conductivity may be a value that is generated by the controller 141 by multiplying the measured conductivity with a value that represents the rate of change of concentration with temperature. In other embodiments, the controller 141 may calculate a concentration directly using a look-up table or formula.

Figure 2B:
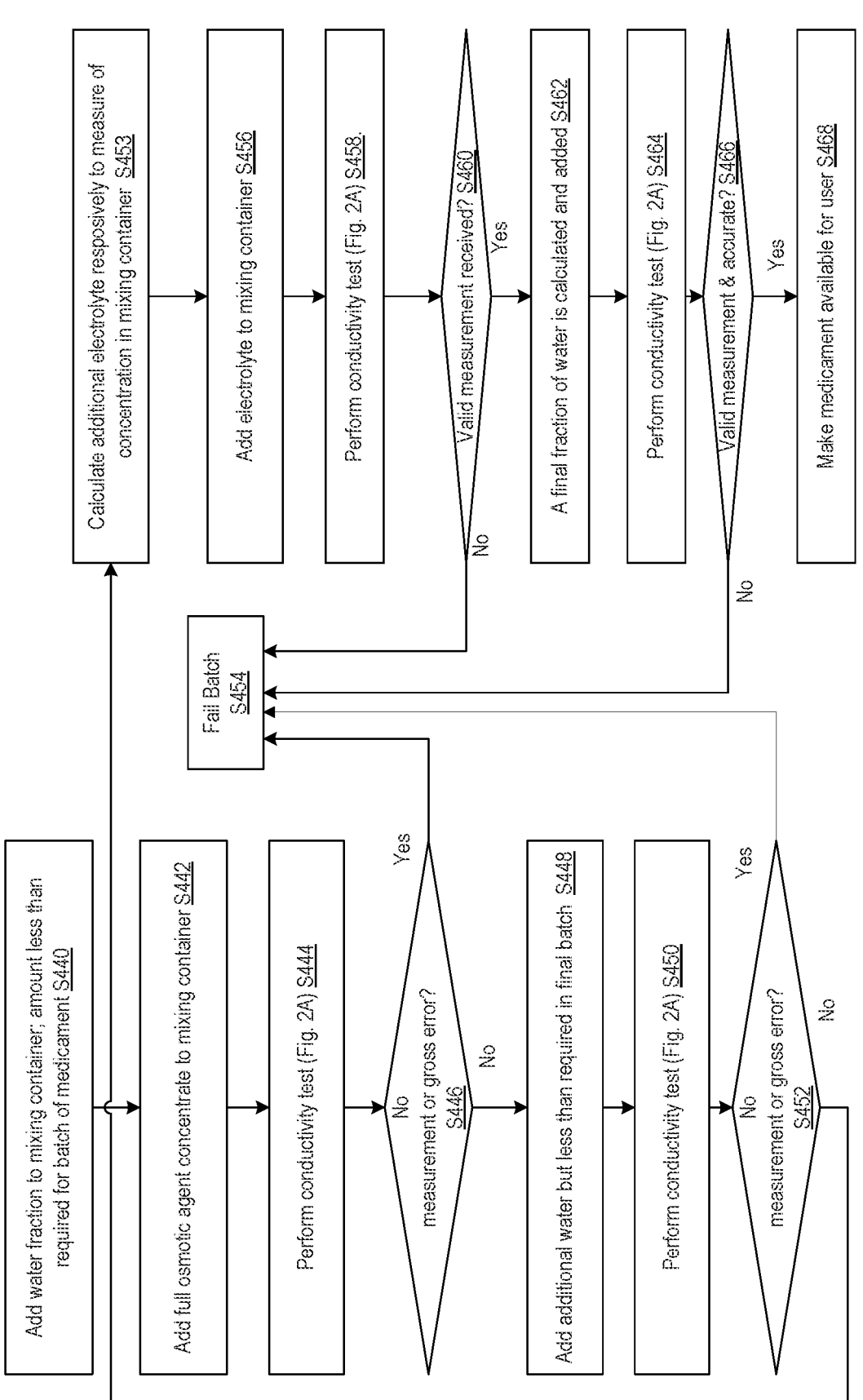
FIG. 2B show a flow chart of a method for preparing a ready-to-use medicament according to embodiments of the disclosed subject matter.

FIG. 2B shows a flow chart for a procedure that may be executed by the controller 141 to generate medicament. It incorporates the procedure of FIG. 2A by the reference to "conductivity test" described with reference to the procedure of FIG. 2A. When the conductivity test is referenced it means the procedure of FIG. 2A is entered and upon exiting proceeds to the next procedure element in FIG. 2B.

At S440, water is added to the mixing container 102 in an amount that is a fraction of what is determined (or expected) to be required for a complete batch of medicament. The amount of water conveyed at S440 may be a fraction of the total estimated amount of water required for a sufficient level of dilution, such as 50% of the expected total water volume.

Figure 4C:
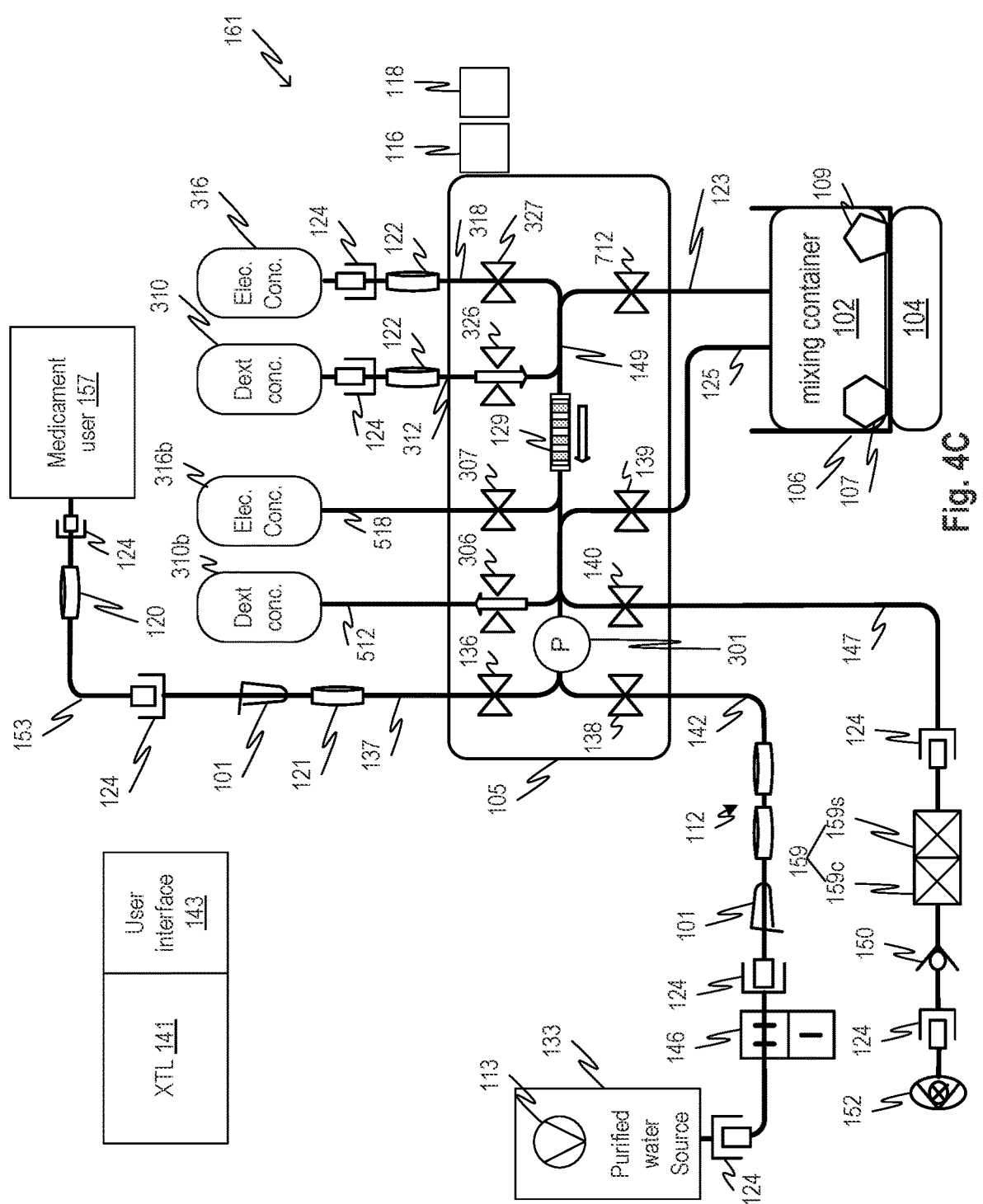
FIG. 4C shows a configuration of the system conveying one medicament concentrate from a multi-day container to a pre-attached daily use container according to embodiments of the disclosed subject matter.

As a subpart of S440, or before S440, a quantity of concentrated medicament is conveyed from multi-use container 310 into daily use container 310*b*. The configuration of the fluid circuit during this operation is shown in FIG. 4C. In embodiments, the concentrated medicament is a concentrated osmotic agent, such as dextrose concentrate or glucose concentrate. As shown in FIG. 4C, the peristaltic pump 129 operates in the direction shown in the figure to pull concentrate from multi-day container 310, through line 312, through sterilizing filter 122, and eventually to daily use container 310*b*. Valves 326 and 306 are opened during this operation, while all other valves are closed. Because peristaltic pump 129 draws a concentrated medicament, which may have a relatively high viscosity, through a sterilizing filter, the upstream side of the pump may experience a negative pressure. Under these conditions, the metering of the quantity of the concentrated medicament may be below an acceptable level of accuracy. The controller 141 may control pump 129 to stop pumping when the daily use container 310*b* is filled to its capacity. Pressure sensor 301 will observe an increase in pressure when daily use container 310*b* is full, and based on this observed increase in pressure, the controller 141 may command pump 129 to stop pumping. In embodiments, controller 141 may command pump 129 to rotate by a specific number of rotations while filling daily use container 310*b* with concentrated medicament, or to operate at a particular speed for a predetermined amount of time.

Figure 4D:
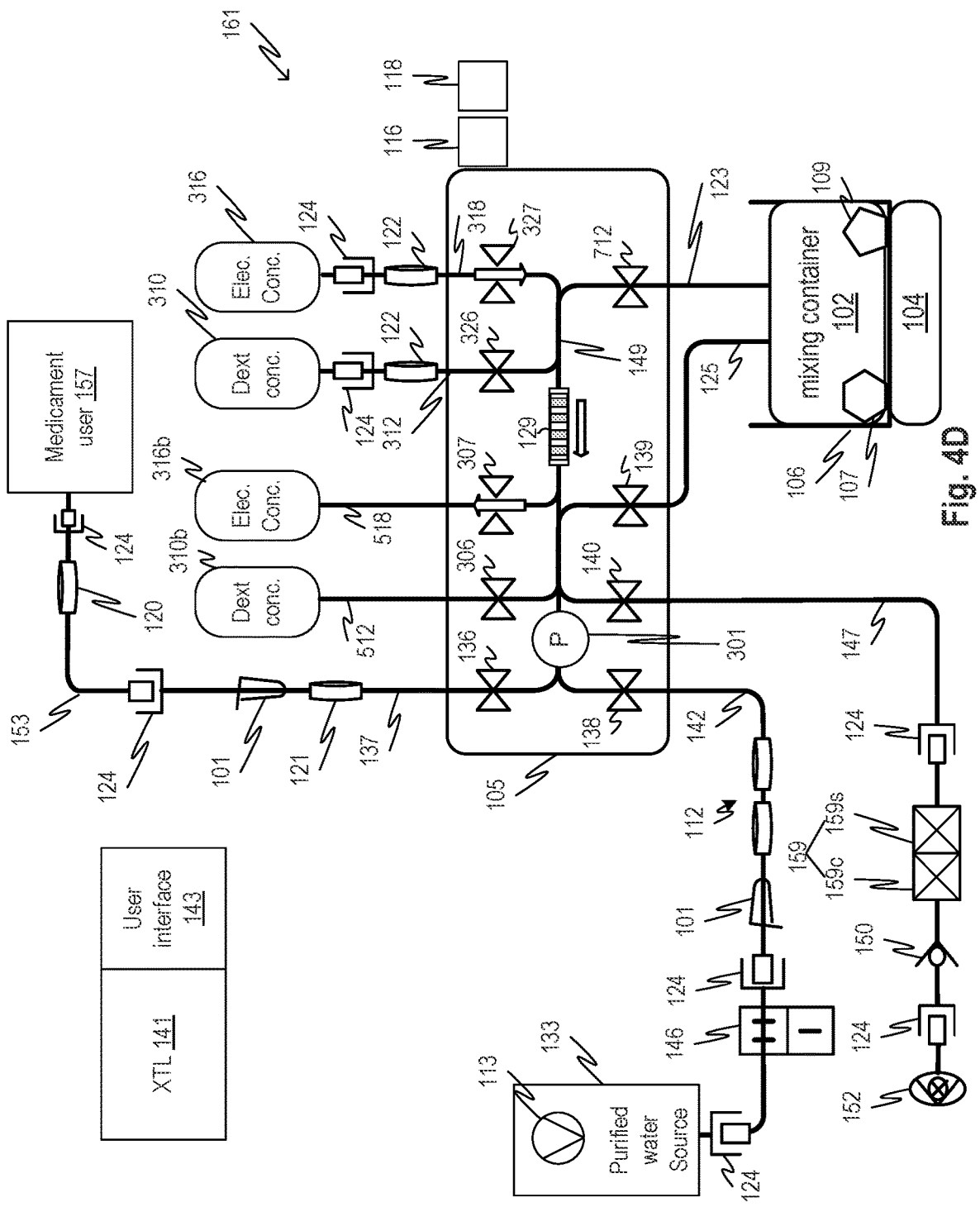
FIG. 4D shows a configuration of the system conveying another medicament concentrate from a multi-day container to a pre-attached daily use container according to embodiments of the disclosed subject matter.

As an additional subpart of S440, or before S440, a quantity of a second concentrated medicament is conveyed from multi-day container 316 into daily use container 316*b*. The configuration of the fluid circuit during this operation is shown in FIG. 4D. In embodiments, the concentrated medicament is a concentrated electrolyte. As shown in FIG. 4D, the peristaltic pump 129 operates in the direction shown in the figure to pull concentrate from multi-day container 316, through line 318, through sterilizing filter 122, and eventually to daily use container 316*b*. Valves 327 and 307 are opened during this operation, while all other valves are closed. Because peristaltic pump 129 draws a concentrated medicament, which may have a relatively high viscosity, through a sterilizing filter, the upstream side of the pump may experience a negative pressure. Under these conditions, the metering of the quantity of the concentrated medicament may be below an acceptable level of accuracy. The controller 141 may control pump 129 to stop pumping when the daily use container 316*b* is filled to its capacity. Pressure sensor 301 will observe an increase in pressure when daily use container 316*b* is full, and based on this observed increase in pressure, the controller 141 may command pump 129 to stop pumping. In embodiments, controller 141 may command pump 129 to rotate by a specific number of rotations while filling daily use container 316*b* with concentrated medicament, or to operate at a particular speed for a predetermined amount of time.

Water is added by pumping it into the mixing container 102 from the purified water source 133. This is done by placing the system in the configuration of FIG. 4A or 4B. The water pump 113 and the peristaltic pump 129 are activated for a predefined number of cycles or a predefined time interval, resulting in a quantify of water being conveyed along water line 142, through opened valve 138, through transfer line 149, through peristaltic pump 129 and through inlet line 123 into mixing container 102.

In an embodiment, the entire quantity of osmotic agent concentrate from container daily use 310*b* is transferred to the mixing container 102 at S442. The fluid circuit takes on the configuration shown in FIG. 5A by controlling valves 306 and 712 to open and operating the peristaltic pump 129 in the forward direction as shown by the arrow under the pump 129 in FIG. 5A. Because there is no filter in the flow path of the concentrate from daily use container 310*b* to mixing container 102, the pressure upstream of pump 129 is not negative (in contrast with the situation described above with multi-day container 310), which increases the metering accuracy of the pump 129.

Figure 6A:
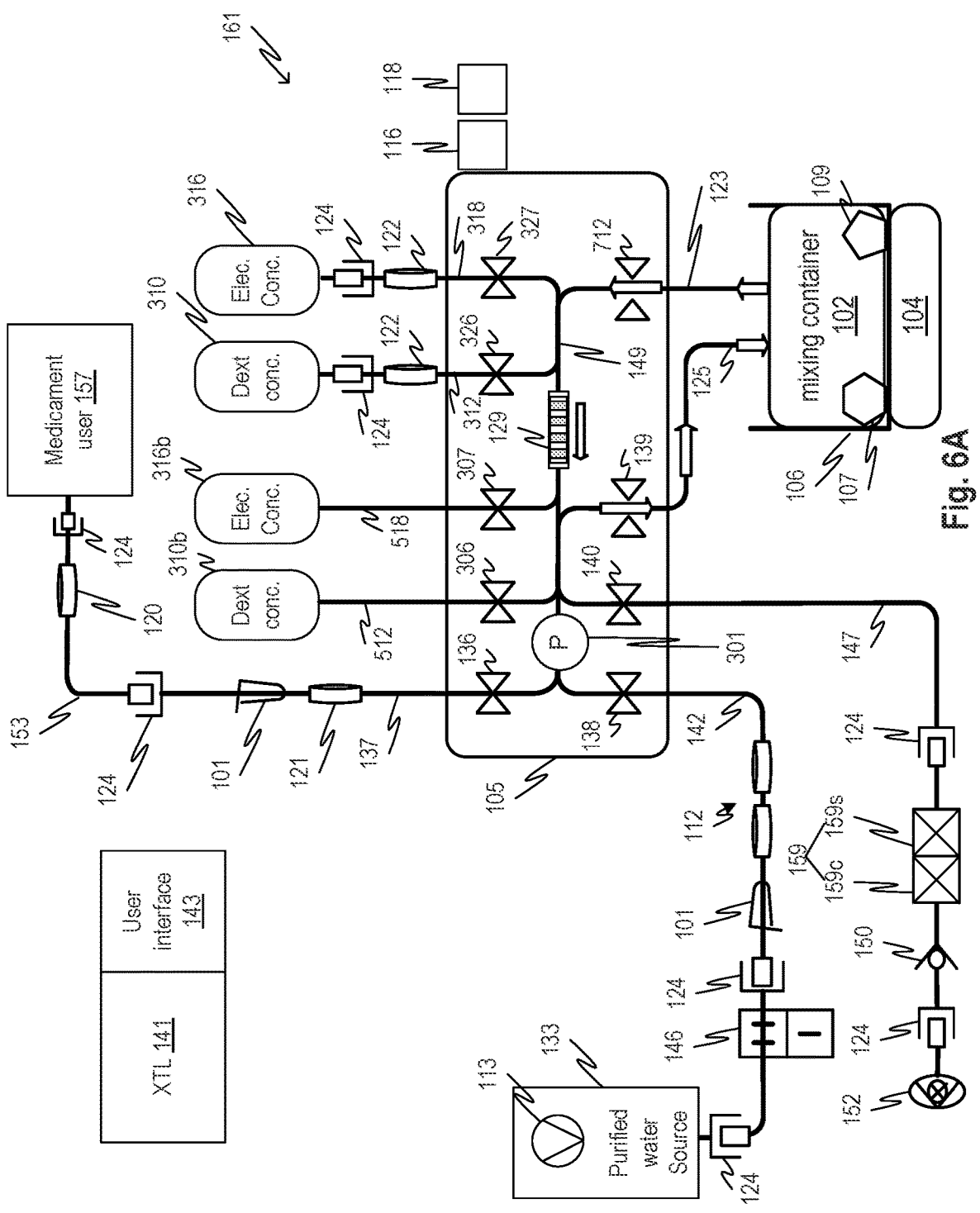
FIG. 6A shows configurations of the systems mixing the content of the mixing container according to embodiments of the disclosed subject matter.
Figure 7:
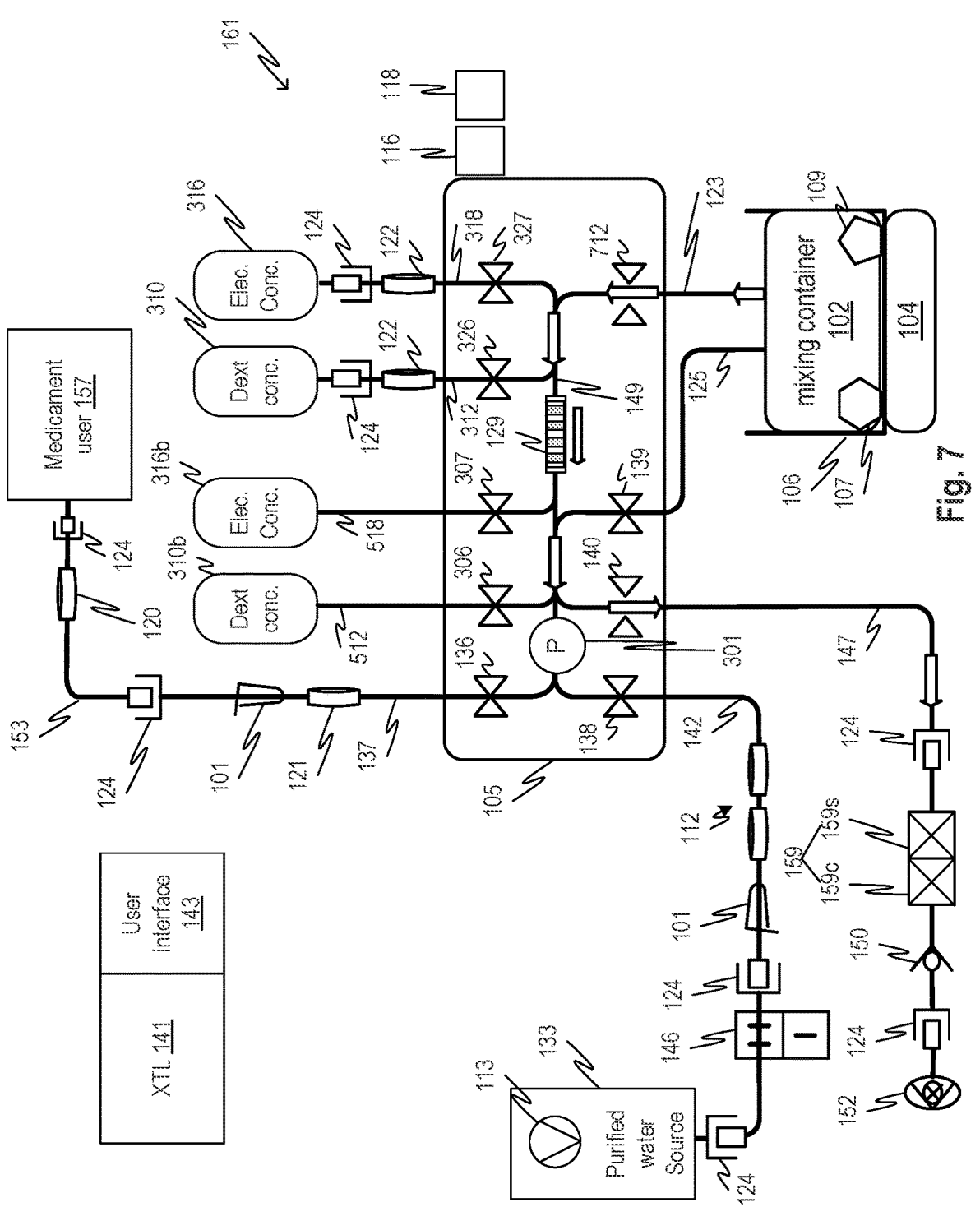
FIG. 7 shows various configurations of the systems testing conductivity of the content of the mixing container according to embodiments of the disclosed subject matter.

Then the contents of the mixing container 102 are mixed by placing the fluid circuit into the configuration shown in FIG. 6A. In other embodiments, less than the entire quantity of osmotic agent concentrate from daily use container 310*b* is conveyed to the mixing container 102, leaving a quantity of the concentrate in the container 310*b* sufficient for making additional batches of dialysate in the future.

The conductivity test described above and illustrated in FIG. 2A is then performed at S444. If an output of gross error or no measurement is received at S446, then the batch is failed at S454. If a measurement is output control proceeds to S448 and additional water is added to the mixing container 102 short of the final amount required to achieve a batch that is usable for the medicament, and the contents of the mixing container 102 is mixed again as described above.

The conductivity test is performed again at S450 and if an output of gross error or no measurement is received at S452 then the batch is failed at S454.

Otherwise, an amount of electrolyte is calculated at S453, based on the conductivity measurement received at S452. Because the osmotic agent and the electrolyte concentrate are provided in separate containers 310*b* and 316*b*, it is possible to generate customized batches of medicament (e.g., dialysate) based on a prescription that is customized for a specific patient. It is also possible to generate smaller quantities of diluted medicament than in a situation where all of the concentrated medicament from daily use containers 310*b* and 316*b* were to be used at once, which allows for a fast walkup time (e.g., less than 1 hour) so a patient can initiate preparation of medicament and then begin therapy in less than an hour.

After the calculation at S453, the appropriate amount of electrolyte concentrate is added to the mixing container 102 at S456. The fluid circuit is placed into the configuration illustrated in FIG. 5B. As shown in the figure, valves 307 and 712 are opened and the peristaltic pump 129 operates in the forward direction to convey the electrolyte concentrate from container daily use 316*b* into mixing container 102. It will be appreciated that because the same pump 129 is used for metering both the osmotic agent concentrate from daily use container 310*b* and the electrolyte concentrate from daily use container 316*b*, the accuracy of the metering is increased, allowing for high precision in establishing the desired custom concentration of the medicament. Moreover, pumping concentrate from daily use container 316*b* avoids pumping through a filter, which further increases metering accuracy as described above. Once all of the electrolyte concentrate required for that particular batch of medicament (e.g., dialysate) is added, the contents of the mixing container 102 are mixed again as described above (See FIG. 6A).

At S458 the conductivity test is performed again and if a valid measurement is not received at S460, then the batch is failed at S454. If the measurement is received, then at S462 a final fraction of water is then calculated based on the valid measurement and added to the mixing container 102 by placing the fluid circuit into a configuration as shown in FIG. 4A or 4B. Then, the contents of the mixing container 102 are mixed again as described above.

The conductivity test is performed again at S464. If the measurement is valid at S466, then the batch is made available for use at S466. Otherwise, the batch is failed at S454. When the batch is made available, the fluid circuit is configured into the configuration shown in FIG. 8A or 8B, and described below.

Figure 3:
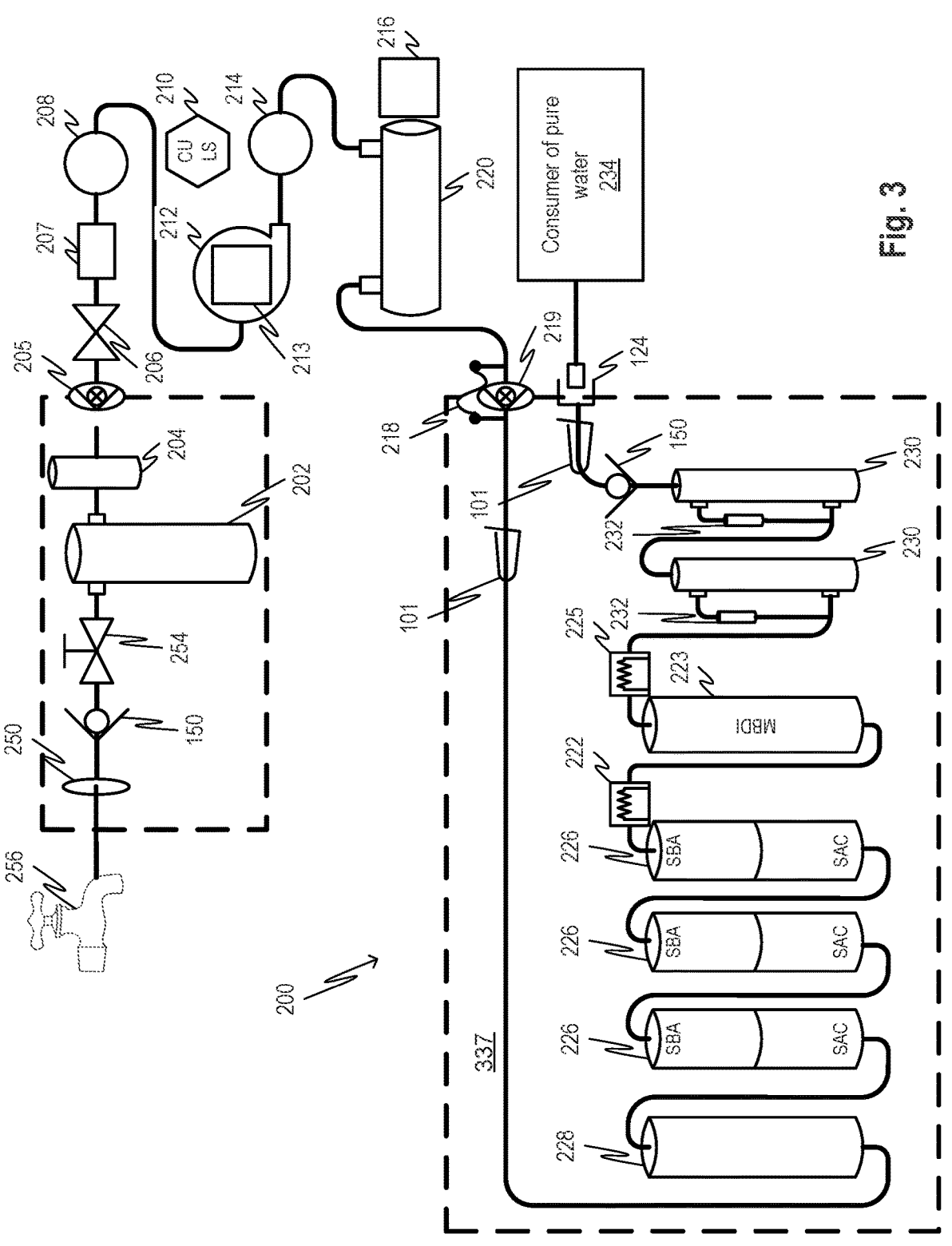
FIG. 3 shows a system for generating purified water for the system and method of FIG. 1A according to embodiments of the disclosed subject matter.

FIG. 3 shows a water treatment plant 200 that may constitute an embodiment the purified water source 133. The water treatment plant 200 has an initial pretreatment stage that includes a connector 250 to connect to an unfiltered water source 256, for example a water tap. The water flows through a check valve 150, through a pressure regulator 254, and then through a sediment filter 202. The check valve 150 prevents backflow of the water. The water then flows through an air vent 204 that removes air from the water. The water then flows through a connector 205 that connects to a water shutoff clamp 206, a snubber 207, and a water inlet pressure sensor 208. Water is pumped by water pump 212 which has an encoder 213 for precise tracking of the water pump 212 speed. The snubber 207 reduces pressure fluctuations. The water then flows through a water output pressure sensor 214, through an ultraviolet light lamp 220 and into a filter plant 337 that performs deionization, carbon filtration, and sterilizing filtration. A UV (ultra violet) light sensor 216 may be provided to detect whether the ultraviolet light lamp 220 is operating, so that it can be replaced if it becomes inoperable. A first-use-fuse 218 together with a connector 219 is provided on the inlet of sterilizing filter plant 337, such that the fuse indicates whether the filter plant 337 has been used. This helps reduce the likelihood that a previously-used filter plant is reused unintentionally. A combined control unit and leak sensor are indicated at 210. In the sterilizing filter plant 337, the water flows through a carbon filter 228 and three separated bed deionization filters 226 which may be resin separated bed filters. The water then flows through a mixed bed deionization filter 223, which follows the separated bed filters 226. The mixed bed deionization filter 223 may be a resin mixed bed filter. Thereafter, the water flows through first and second ultrafilters 230, which follow the mixed bed deionization filter 223, and into the consumer of pure water 234. The embodiment of FIG. 1A is an example of a consumer of pure water 234.

Between a last separated bed deionization filter 226 and the mixed bed deionization filter 223 is a resistivity sensor 222 which indicates when the separated bed deionization filters 226 are nearing exhaustion, or at exhaustion. The mixed bed deionization filter 223 is still able to hold a predefined minimum magnitude of resistivity but the separated bed deionization filters 226 and the mixed bed deionization filter 223 may be replaced at the same time. In embodiments, along with the separated bed deionization filters 226 and the mixed bed deionization filter 223, the carbon filter 228 and ultrafilters 230 along with the interconnecting lines and other components may also be replaced as a single package. A current treatment can be completed in reliance on the mixed bed deionization filter 223 before the exhausted filters are replaced. A further resistivity sensor 225 detects unexpected problems with the mixed bed deionization filter 223 upstream from the separated bed deionization filters 226, which may require shutdown of the treatment and immediate replacement of the filters. Note that each of the ultrafilters 230 has an air vent 232. A check valve 150 is located downstream of the ultrafilters 230. The consumer of pure water 234 may be unit such as that of FIG. 1A which mixes a batch of medicament for use by a medicament user 157 such as a peritoneal dialysis cycler or any other type of medicament consuming device.

It should be evident from the above that the procedures of FIG. 2B in combination with those of FIG. 2A may be performed using the embodiment of FIG. 1A.

Note in any of the embodiments where the term clamp is used, it should be recognized that the functional element includes a tube or other flexible conduit and the clamp so that it functions as a valve. In any of the embodiments, another type of valve may be substituted for the clamp and conduit to provide the same function. Such a variation may be considered to alternative embodiments and clamp and conduit are not limiting of the subject matter conveyed herein.

Note that in any of the embodiments that identify the bag as the container, any bag may be replaced by any container including those of glass, polymer and other materials. In any embodiment where flow control is performed by a clamp, it should be understood that in any embodiment, including the claims, any clamp can be replaced by another type of valve such as a stopcock valve, a volcano valve, a ball valve, a gate valve or other type of flow controller. It should be understood that a clamp in the context of the disclosed subject matter is a clamp that closes around a tube to selectively control flow through the position of the clamp. Note that in any of the embodiments, the order of adding and mixing to the mixing container 102 can by reversed from what is described with respect to the embodiments. In any of the embodiments instead of dextrose concentrate being used, this can be substituted for glucose or another osmotic agent.

The process of providing purified water from the purified water source 133 is described next. As shown in FIG. 4A, water inlet clamp 138 is opened and the water pump 113 operates to convey purified water along water line 142. Valve 139 can be opened so that the water pump 113 alone, without the involvement of peristaltic pump 129 conveys water into the mixing container 102 through line 125. Alternatively, valve 139 can be closed and peristaltic pump 129 operates to move water from transfer line 149 to inlet line 123 and through that into mixing container 102. In this situation, pump 113 provides a positive upstream pressure for the peristaltic pump 129 and valve 712 is opened, as shown in FIG. 4B.

Referring to FIG. 4B, water is provided from the purified water source 133 to the system. The peristaltic pump 129 is configured to move fluid in a line 123 connected to the mixing container 102. The peristaltic pump 129 also moves fluid, at selected times, through the line 125 which returns the fluid to the mixing bag. Initially the purified water from the purified water source 133 is pumped by the water pump 113 with water inlet clamp 138 open and the batch release clamp 136 and the conductivity sensor clamp 140 closed such that water is pumped into the mixing container 102 through line 123 with the peristaltic pump 129 running so as to convey water into the mixing container 102, as shown in FIG. 4B.

In the configuration of FIG. 4B, the peristaltic pump 129 rotates in the same direction as when it conveys concentrate from daily use containers 310b and 316b, which increase metering accuracy. The peristaltic pump 129 can be calibrated and the calibration will apply to all fluids conveyed by the pump when the pump operates in the same direction. The calibration operation may take place before pump 129 is used to convey concentrate and water into mixing container 102. In embodiments, after the calibration, pump 129 is not operated in the reverse direction until all metering for a particular batch of medicament is completed. In embodiments, the pump 129 may be calibrated after the pump is operated in the reverse direction, before the pump is used for metering concentrate and water for a batch of medicament.

Figure 5A:
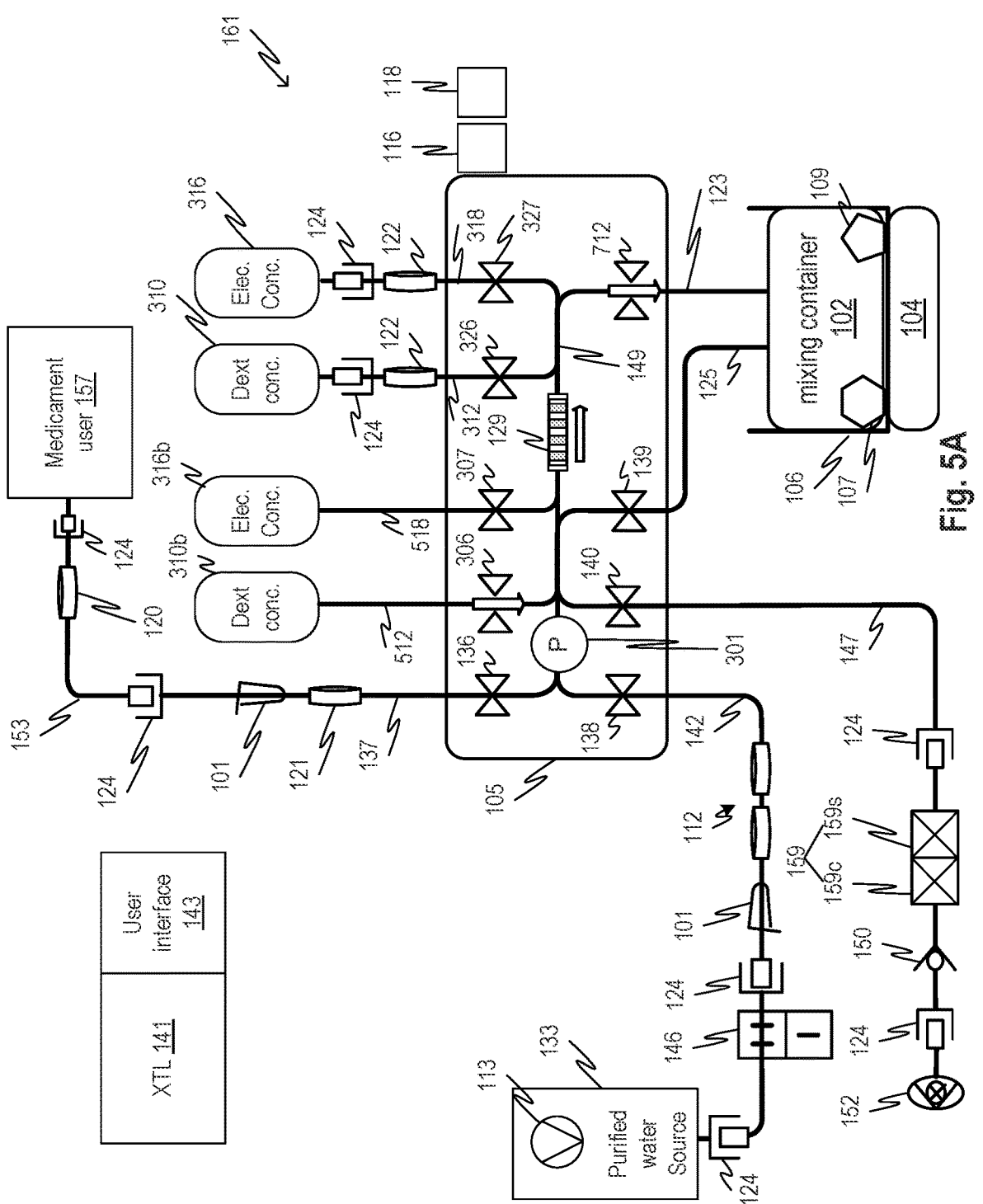
FIGS. 5A and 5B show configurations of systems providing various types of medicament concentrate from daily use containers to the mixing container according to embodiments of the disclosed subject matter.

FIG. 5A illustrates the configuration of the system when the osmotic agent concentrate is conveyed from daily use container 310b (e.g., dextrose, glucose, etc.) through osmotic supply line 512 and eventually into the mixing container 102. As shown in the figure, valve 306 and valve 712 are opened and peristaltic pump 129 can operate in in the direction shown (pictured to the right on the drawing sheet), such that the osmotic concentrate flows from daily use container 310b through inlet line 123 into mixing container 102. This is the same direction as used when metering water and electrolyte concentrate, which can improve relative accuracy in the metering. The peristaltic pump 129 can be controlled to precisely meter a desired quantity of the osmotic concentrate into mixing container 102. In embodiments, only a fraction of the total quantity of the osmotic agent concentrate present in its container 310b is provided into mixing container 102, such that multiple batches of the medicament can be prepared in the mixing container 102 from a single container 310b; and each of the batches can be customized based on a desired concentration to create custom mini batches. In embodiments, all concentrate from daily use container 310b is conveyed into the mixing container 102.

In an alternate embodiment, the osmotic concentrate 310b can be positioned sufficiently high or above mixing container 102 that a gravity powered fill can be accomplished. In this scenario, valve 306 is opened and valve 139 is opened (not illustrated in FIG. 5A) which permits gravity to convey the osmotic agent concentrate through inlet line 125 into mixing container 102, without the use of peristaltic pump 129. In embodiments, the entirety of the osmotic agent concentrate 310b is allowed to flow into the mixing container 102 so that the quantity of the osmotic agent concentrate that is present in the mixing container 102 is known based on the original amount of the osmotic agent concentrate that was present in its container 310b.

Figure 5B:
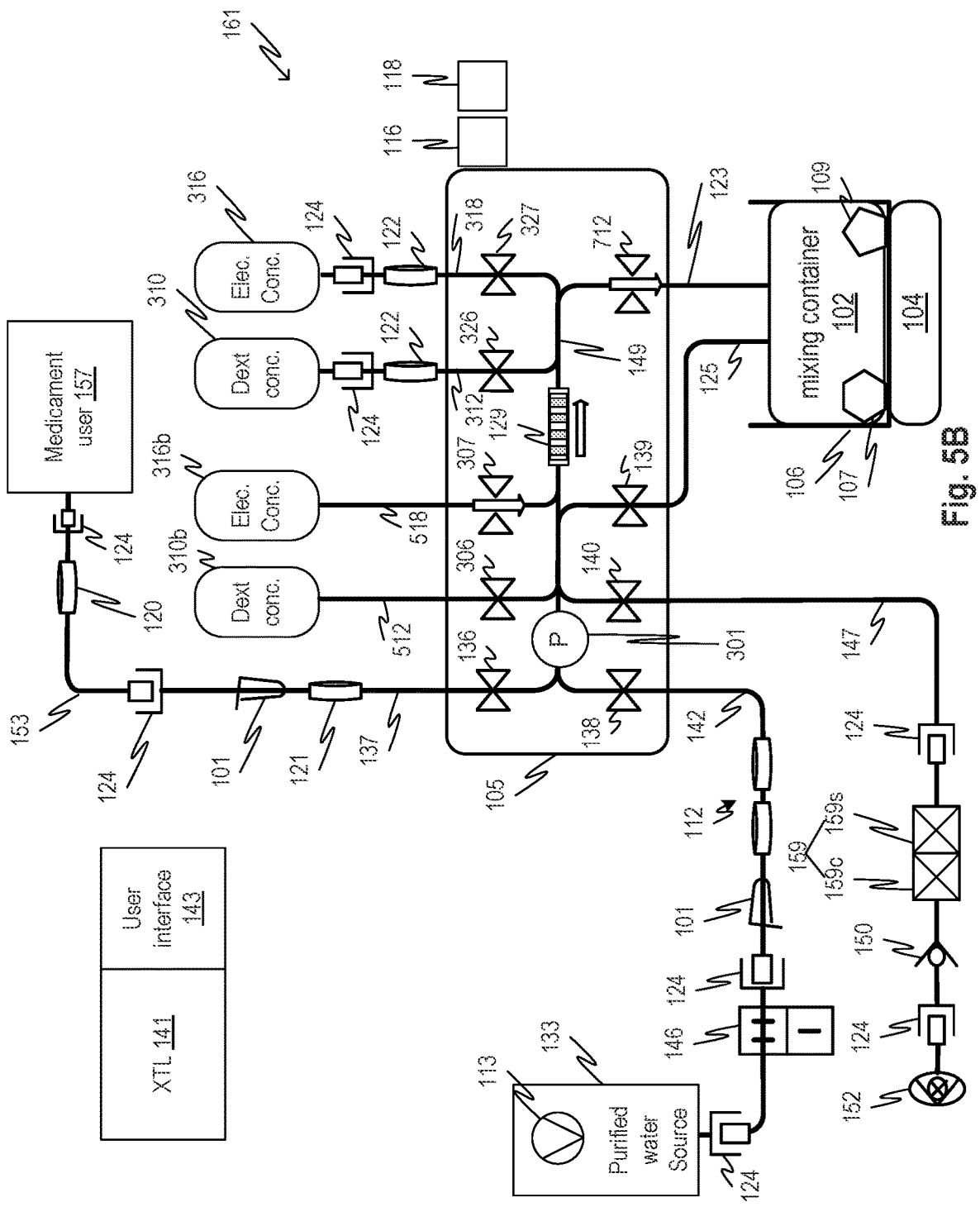

FIG. 5B illustrates the configuration of the system when the electrolyte concentrate flows from daily use container 316b through electrolyte supply line 518 and eventually into the mixing container 102. As shown in the figure, valves 307 and 712 are opened and peristaltic pump 129 can operate in in the direction shown (pictured to the right on the drawing sheet), such that the electrolyte concentrate flows through inlet line 123 into mixing container 102. The peristaltic pump 129 can be controlled to precisely meter a desired quantity of the electrolyte concentrate into mixing container 102. In embodiments, only a fraction of the total quantity of the electrolyte concentrate present in daily use container 316b is provided into mixing container 102, such that multiple batches of the medicament can be prepared in the mixing container 102; and each of the batches can be customized based on a desired concentration to create custom mini batches.

In an alternate embodiment, the electrolyte concentrate 316b can be positioned sufficiently high or above mixing container 102 that a gravity powered fill can be accomplished. In this scenario, valve 307 is opened and valve 139 is opened (not illustrated in FIG. 5B) which permits gravity to convey the electrolyte concentrate through inlet line 125 into mixing container 102, without the use of peristaltic pump 129. In embodiments, the entirety of the electrolyte concentrate 316b is allowed to flow into the mixing container 102 so that the quantity of the electrolyte concentrate 316b that is present in the mixing container 102 is known based on the original amount of the electrolyte concentrate that was present in its initial container.

Referring to FIG. 6A, to mix the contents of the mixing container 102 the peristaltic pump 129 pumps fluid in a circular path through lines 123 and 125 in a direction designated with an arrow in the figure (to the left in the figure) with all the clamps closed except for clamps 139 and 712 in FIG. 6A. The contents of the mixing container 102 are mixed by the flow circulating through the mixing container 102. The pumping direction shown in the figure is the reverse direction of those used for metering concentrates and water, and this may have an effect on the calibration of the pump 129. In embodiments, the pump 129 operates in the same direction as when it is used for metering components to avoid or minimize effects on the calibration of the pump.

Referring to FIG. 7, after a sufficient time of mixing, a sample of the fluid in the mixing container 102 may be pumped through a drain conductivity line 147 which contains conductivity/temperature sensors 159c and 159s (control sensor 159c and safety sensor 159s) to determine a temperature-compensated conductivity of the diluted medicament. Each sensor 159c and 159s may be configured to calculate conductivity and temperature of fluid passing through or past the sensor. Two redundant sensors 159c and 159s may be provided, to enable a comparison of their respective measurements and thereby to confirm that the sensors are functioning. If their respective measurements are within a predetermined range, the sensors are understood to be functioning correctly. On the other hand, if their respective measurements are outside of the predetermined range, an error condition may be signaled as described below. Although two separate sensors 159c and 159s are shown, a single sensor 159 may be provided instead, and multiple readings may be taken over time to generate multiple values for comparison and to determine the proper functioning of the sensor 159.

Valve 140 is opened and the peristaltic pump 129 operates in reverse direction as shown in the figure to covey fluid from the mixing container 102 toward the conductivity sensor(s) 159. A check valve 150 prevents backflow of fluid from the drain connection 152. In FIG. 7, the fluid channel that contains the conductivity sensor(s) 159 may be provided with connectors 124, as shown, so that the whole fluid channel can be replaced as needed if the accuracy of the conductivity sensor(s) 159 degrades or indicates a failure.

After the conductivity test is completed, but before supplying medicament from the mixing container 102 to the medicament user 157, a quantity of concentrated medicament from multi-day container 310 and/or multi-day container 316 may be pumped into drain line 147. In embodiments, valves 140 and 326 are opened while all others are closed, and the peristaltic pump 129 operates in the reverse direction (relative to the direction when metering components of the medicament) and conveys a quantity of concentrate from multi-day container 310 into the drain line. The pump 129 may operate until a conductivity reading from sensor 159 indicates that the concentrate has reached the sensor. The pump 129 may operate a period of time longer than the detection, to ensure that the concentrate has reached drain connection 152. Although the above was described with reference to multi-day concentrate container 310, it will be appreciated that concentrate from multi-day concentrate container 316 may be used instead or in addition. In this case, valves 140 and 327 are opened, while all other valves are closed. Concentrated medicament may inhibit growth of pathogens, such as bacteria, in the drain line. Once sufficient concentrated medicament is pumped into the drain line 147, valve 140 is closed and the check valve 150 together with valve 140 hold the concentrate in the drain line until the concentrate is flushed out during a drain operation.

Figure 8A:
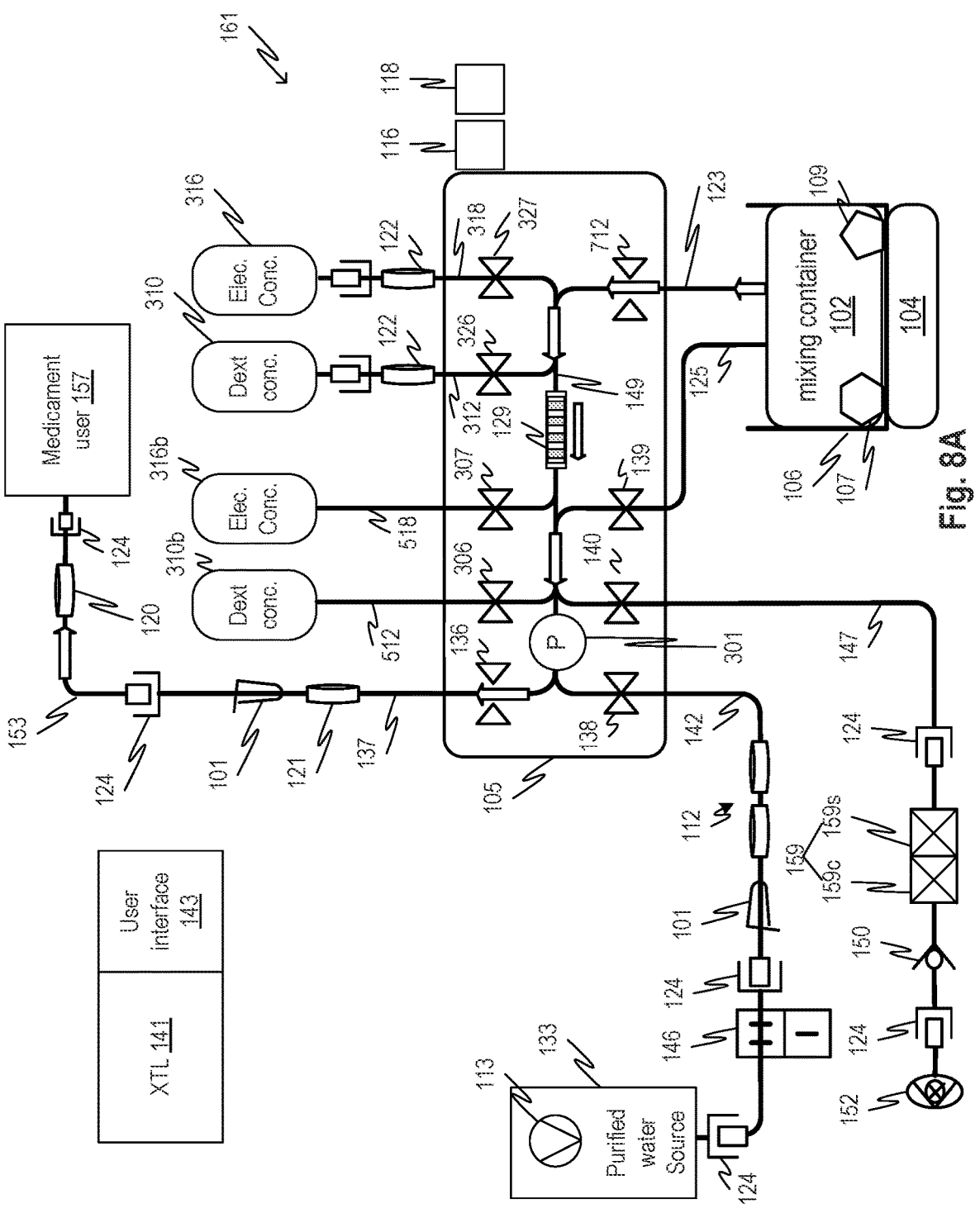
FIGS. 8A and 8B show configurations of the system providing the content of the mixing container to a consumer of the content according to embodiments of the disclosed subject matter.
Figure 8B:
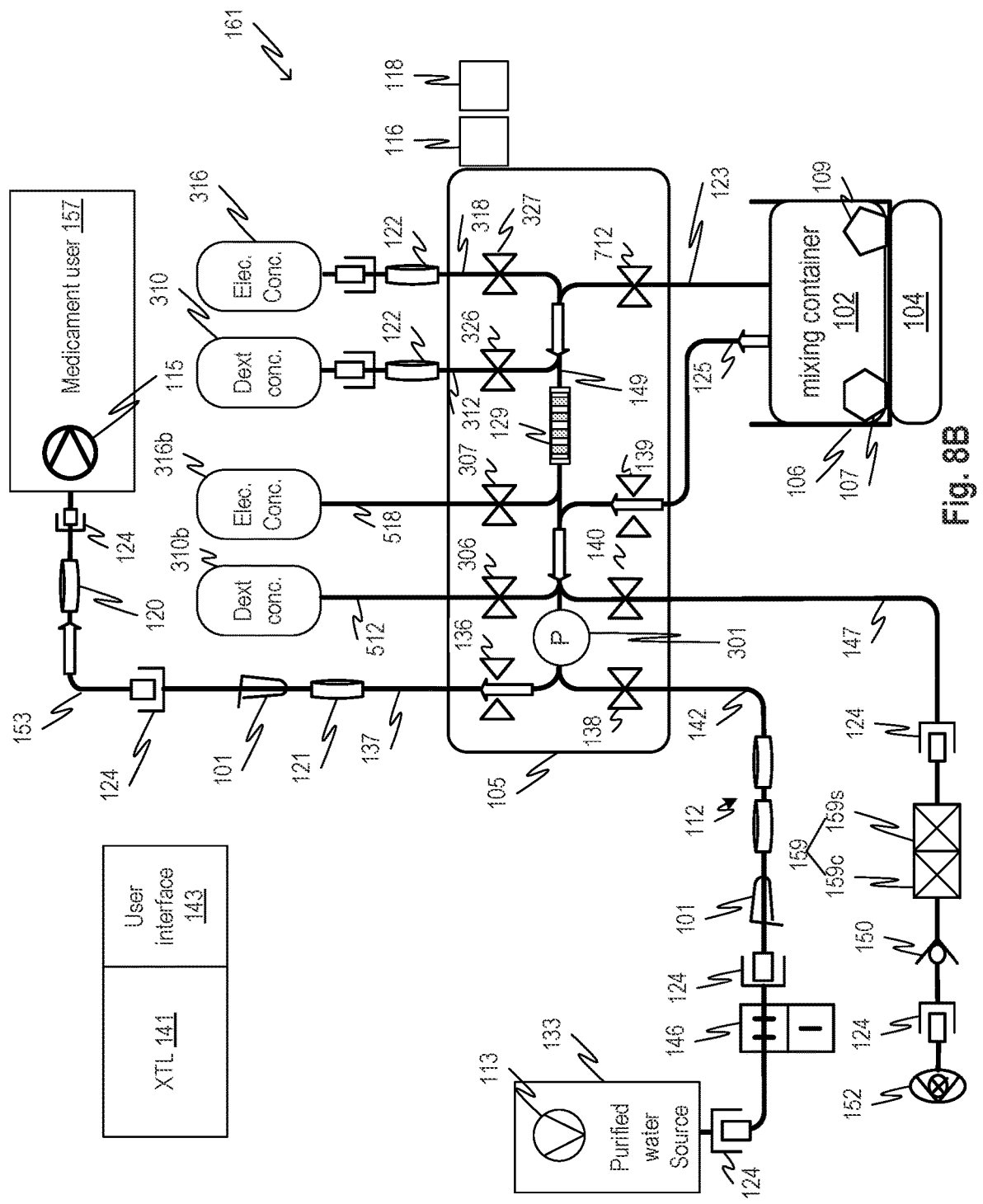

Referring now to FIGS. 8A and 8B, once of the medicament is prepared and mixed in the mixing container at 102, and the medicament is deemed to be ready for use based on conductivity checks described above, the medicament is provided to the medicament user 157. FIGS. 8A and 8B illustrate various arrangements of the fluid circuit for providing the medicament. At this time, the water inlet clamp 138 and the conductivity sensor clamp 140 are closed. The medicament user 157 may be any type of treatment device or container that receives the mixed medicament from the mixing container 102.

The batch release clamp 136 and inlet line valve 712 are open and the water inlet clamp 138 and the conductivity sensor clamp 140 are closed. The pump 115 in a medicament user 157 may then draw fluid from the circular path as the peristaltic pump 129 rotates to maintain fluid at a pressure that is controlled based on a pressure signal from pressure sensor 301, in FIG. 8A.

The medicament pump 115 in the medicament user 157 may see a positive pressure due to the operation of peristaltic pump 129, which mimics the pressure of an elevated medicament container with a head pressure. In embodiments, clamp 139 is closed while peristaltic pump 129 operates in the direction shown in the drawing. Clamp 136 and 712 is opened, and the medicament is conveyed through medicament supply lines 137 and 153 to medicament user 157. A pressure sensor 301 is provided to measure the pressure in this fluid channel and to provide a signal, which may be used in feedback control, to modulate the speed of the peristaltic pump 129 and thereby provide a predetermined pressure in the formed fluid channel.

In further embodiments illustrated in FIG. 8B, the peristaltic pump 129 is not used, and instead medicament user pump 115 operates to draw the medicament from the mixing container 102. Clamp 139 and clamp 136 are both opened, thereby providing a fluid path between the mixing container 102 and the medicament user 157. It is possible to elevate mixing container 102 to such a level that it provides a positive pressure (head pressure) for the medicament user 157.

Figure 9:
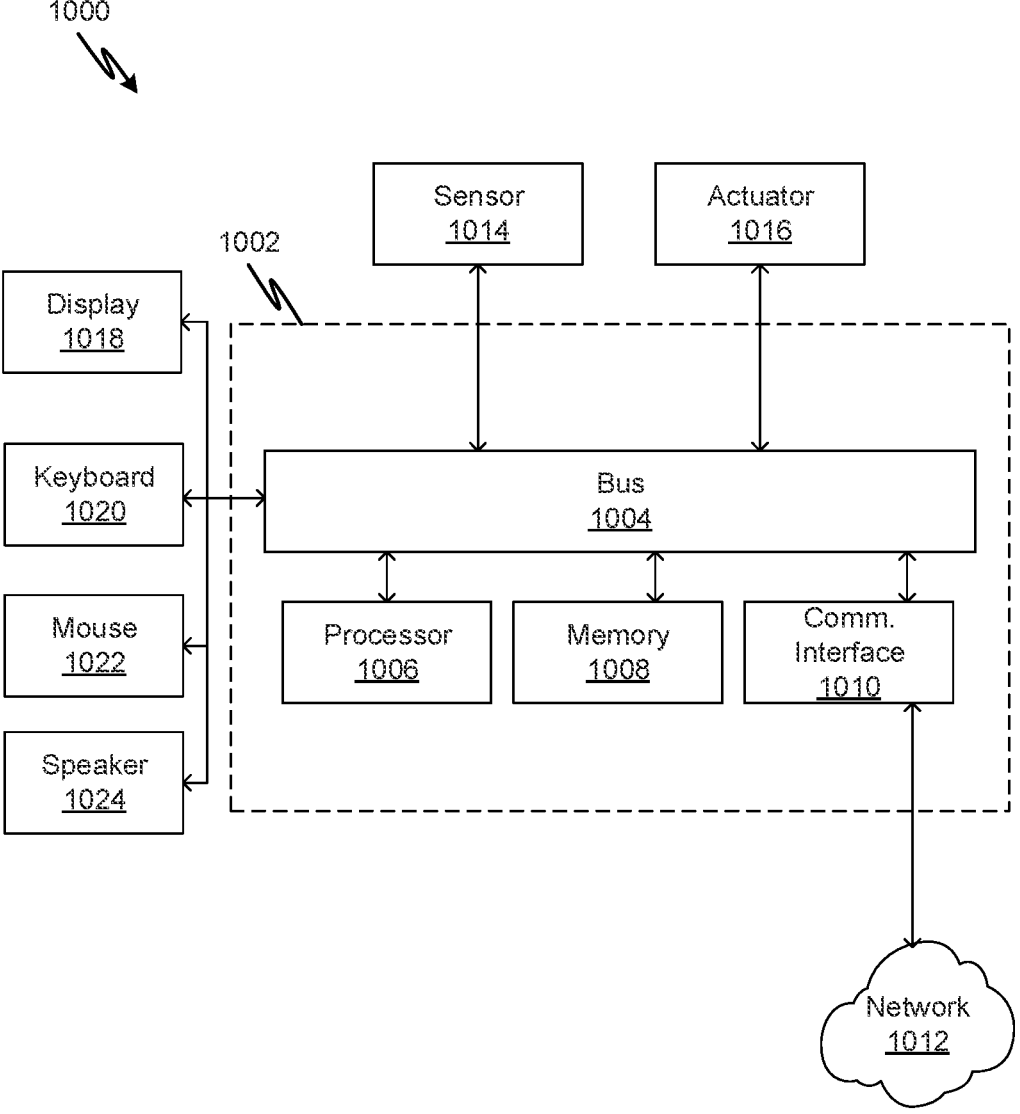
FIG. 9 shows a computer system that may describe the functions and elements of a controller as described herein and in accordance with the embodiments of the disclosed subject matter.

FIG. 9 shows a block diagram of an example computer system according to embodiments of the disclosed subject matter. In various embodiments, all, or parts of system 1000 may be included in a medical treatment device/system such as a renal replacement therapy system. In these embodiments, all, or parts of system 1000 may provide the functionality of a controller of the medical treatment device/systems. In some embodiments, all, or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with one or more sensors 1014 and one or more actuators 1016, each providing respective functionality in accordance with various embodiments disclosed herein, for example, for measuring signals.

It will be appreciated that the modules, processes, systems, and sections described above can be implemented in hardware, hardware programmed by software, software instruction stored on a non-transitory computer readable medium or a combination of the above. For example, a method for providing a medicament to a medicament user can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems of medical devices and/or computer programming arts.

Moreover, embodiments of the disclosed method, system, and computer program product can be implemented in software executed on a programmed general-purpose computer, a special purpose computer, a microprocessor, or the like.

According to a first further embodiment, there is provided a system for preparing a medicament for use by a medicament user, including: a proportioning machine with a controller and pumping and clamping actuators to engage a fluid circuit having pumping and clamping portions that engage with respective actuators of the proportioning machine; the fluid circuit having an empty mixing container attached to the fluid circuit, a first pre-attached concentrate container, and a second pre-attached concentrate container; a first detachable container having a first concentrated medicament therein; a second detachable container having a second concentrated medicament therein; the proportioning machine being configured to flow fluid from the mixing container into and out of the mixing container to circulate the fluid; the proportioning machine being configured to flow water and the first and second concentrated medicaments into said mixing container to dilute the first and second concentrated medicaments to make a ready-to-use medicament; the controller being configured to regulate a clamp on a return line leading to said mixing container to generate a predefined pressure in an outlet line of the fluid circuit which is attachable to an external user of the ready-to-use medicament; and the predefined pressure being maintained in the outlet line by pressure feedback control.

According to a second further embodiment, there is provided the system of the first further embodiment or any of the other foregoing embodiments, wherein the controller is further configured to control the clamping portions and the pumping and clamping actuators to convey the first concentrate medicament from the first detachable container through a sterilizing filter into the first pre-attached concentrate container. According to a third further embodiment, there is provided the system of the second further embodiment or any of the other foregoing embodiments, wherein the pumping and clamping actuators include a peristaltic pump, and the peristaltic pump operates in a first direction when the peristaltic pump conveys the first concentrated medicament into the first pre-attached concentrate container. According to a fourth further embodiment, there is provided the system of the third further embodiment or any of the other foregoing embodiments, wherein the controller is further configured to control the peristaltic pump to operate in a second direction, opposite to the first direction, when the first concentrated medicament is conveyed into the mixing container. According to a fifth further embodiment, there is provided the system of the fourth further embodiment or any of the other foregoing embodiments, wherein the first concentrated medicament is conveyed from the first pre-attached concentrate container into the mixing container. According to a sixth further embodiment, there is provided the system of the first further embodiment or any of the other foregoing embodiments, wherein the controller is further configured to control the clamping portions and the pumping and clamping actuators to convey the second concentrate medicament from the second detachable container through a sterilizing filter into the second pre-attached concentrate container. According to a seventh further embodiment, there is provided the system of the sixth further embodiment or any of the other foregoing embodiments, wherein the pumping and clamping actuators include a peristaltic pump, and the peristaltic pump operates in a first direction when the peristaltic pump conveys the second concentrated medicament into the second pre-attached concentrate container. According to an eighth further embodiment, there is provided the system of the seventh further embodiment or any of the other foregoing embodiments, wherein the controller is further configured to control the peristaltic pump to operate in a second direction, opposite to the first direction, when the second concentrated medicament is conveyed into the mixing container. According to a ninth further embodiment, there is provided the system of the eighth further embodiment or any of the other foregoing embodiments, wherein the second concentrated medicament is conveyed from the second pre-attached concentrate container into the mixing container. According to a tenth further embodiment, there is provided the system of the fifth further embodiment or any of the other foregoing embodiments, wherein the peristaltic pump operates in the second direction when water is conveyed into the mixing container. According to an eleventh further embodiment, there is provided the system of the ninth further embodiment or any of the other foregoing embodiments, wherein the peristaltic pump operates in the second direction when water is conveyed into the mixing container. According to a twelfth further embodiment, there is provided the system of the first further embodiment or any of the other foregoing embodiments, the controller is configured to control the clamping portions and the pumping and clamping actuators to convey at least one of the first concentrated medicament from the first detachable container and the second concentrated medicament from the second detachable container into a drain line to inhibit bacterial growth in the drain line. According to a thirteenth further embodiment, there is provided the system of the first further embodiment or any of the other foregoing embodiments, wherein the clamp is a controllable clamp that regulates flow and pressure in a line. According to a fourteenth further embodiment, there is provided the system of the first further embodiment or any of the other foregoing embodiments, wherein the first and second concentrated medicaments and ready-to-use medicament are for peritoneal dialysis fluid. According to a fifteenth further embodiment, there is provided the system of the first further embodiment or any of the other foregoing embodiments, wherein the external user of the ready-to-use medicament is a peritoneal dialysis cycler. According to a sixteenth further embodiment, there is provided the system of the first further embodiment or any of the other foregoing embodiments, wherein the mixing container is removably connected to the fluid circuit by connectors. According to a seventeenth further embodiment, there is provided the system of the first further embodiment or any of the other foregoing embodiments, wherein the pumping and clamping actuators include a peristaltic pump actuator. According to an eighteenth further embodiment, there is provided the system of the first further embodiment or any of the other foregoing embodiments, wherein the fluid circuit is connectable to a source of purified water. According to a nineteenth further embodiment, there is provided the system of the first further embodiment or any of the other foregoing embodiments, wherein the fluid circuit is a single-use consumable.

According to a twentieth further embodiment, there is provided a system for preparing a medicament for use by a medicament user, including: a proportioning machine with a controller and pumping and clamping actuators to engage a fluid circuit having pumping and clamping portions that engage with respective actuators of the proportioning machine; the fluid circuit having a sterilized mixing container connected to the fluid circuit; a first concentrate container having a first concentrated medicament therein; a second concentrate container having a second concentrated medicament therein; the proportioning machine being configured to flow fluid from the mixing container into and out of the mixing container to circulate the fluid; the proportioning machine being configured to flow water into said mixing container to dilute the first and second concentrated medicaments to make a ready-to-use medicament; and the first and the second concentrate containers being removably connected to the fluid circuit by connectors.

According to a twenty-first further embodiment, there is provided the system of the twentieth further embodiment or any of the other foregoing embodiments, further including: a third concentrate container pre-attached to the fluid circuit as an empty bag and sterilized together with the fluid circuit. According to a twenty-second further embodiment, there is provided the system of the twenty-first further embodiment or any of the other foregoing embodiments, further including: a fourth concentrate container pre-attached to the fluid circuit as an empty bag and sterilized together with the fluid circuit. According to a twenty-third further embodiment, there is provided the system of the twenty-second further embodiment or any of the other foregoing embodiments, wherein the proportioning machine is configured to flow the first concentrated medicament from the first concentrate container into the third concentrate container before the dilution of the first concentrated medicament in the mixing container. According to a twenty-fourth further embodiment, there is provided the system of the twenty-second further embodiment or any of the other foregoing embodiments, wherein the proportioning machine is configured to flow the second concentrated medicament from the second concentrate container into the fourth concentrate container before the dilution of the second concentrated medicament in the mixing container. According to a twenty-fifth further embodiment, there is provided the system of the twenty-third further embodiment or any of the other foregoing embodiments, wherein the proportioning machine is configured to flow the first concentrated medicament from the third concentrate container into the mixing container before the dilution of the first concentrated medicament in the mixing container. According to a twenty-sixth further embodiment, there is provided the system of the twenty-fourth further embodiment or any of the other foregoing embodiments, wherein the proportioning machine is configured to flow the second concentrated medicament from the fourth concentrate container into the mixing container before the dilution of the second concentrated medicament in the mixing container. According to a twenty-seventh further embodiment, there is provided the system of the twentieth further embodiment or any of the other foregoing embodiments, wherein the proportioning machine is configured to flow at least one of the first concentrated medicament and the second concentrated medicament from the first concentrate container and/or from the second concentrate container into a drain line to inhibit growth of pathogens in the drain line. According to a twenty-eighth further embodiment, there is provided the system of the twentieth further embodiment or any of the other foregoing embodiments, wherein the first and second concentrated medicaments and ready-to-use medicament are for peritoneal dialysis fluid. According to a twenty-ninth further embodiment, there is provided the system of the twentieth further embodiment or any of the other foregoing embodiments, wherein the medicament user of the ready-to-use medicament is a peritoneal dialysis cycler. According to a thirtieth further embodiment, there is provided the system of the twentieth further embodiment or any of the other foregoing embodiments, wherein the controller is configured to regulate a clamp on a return line leading to said mixing container to generate a predefined pressure in an outlet line of the fluid circuit which is attachable to an external user of the ready-to-use medicament, wherein the predefined pressure is maintained in the outlet line by pressure feedback control. According to a thirty-first further embodiment, there is provided the system of the thirtieth further embodiment or any of the other foregoing embodiments, wherein the clamp is a controllable clamp that regulates flow and pressure in a line. According to a thirty-second further embodiment, there is provided the system of the twentieth further embodiment or any of the other foregoing embodiments, wherein the pumping and clamping actuators include a peristaltic pump actuator. According to a thirty-third further embodiment, there is provided the system of the twentieth further embodiment or any of the other foregoing embodiments, wherein the fluid circuit is connectable to a source of purified water. According to a thirty-fourth further embodiment, there is provided the system of the twentieth further embodiment or any of the other foregoing embodiments, wherein the fluid circuit is a single-use consumable.

According to a thirty-fifth further embodiment, there is provided a method of generating a custom mini batch of dialysate with a proportioning system, including: attaching a disposable component to the proportioning system; generating purified water with a water purification system; adding a first quantity of the purified water to a mixing container that is pre-attached to the disposable component; conveying a second quantity of a first concentrated medicament to the mixing container; first mixing contents of the mixing container; determining a concentration of the contents of the mixing container; conveying a third quantity of a second concentrated medicament to the mixing container; second mixing the contents of the mixing container; confirming a final concentration of the contents of the mixing container; and providing the contents of the mixing container to a medicament user.

According to a thirty-sixth further embodiment, there is provided the method of the thirty-fifth further embodiment or any of the other foregoing embodiments, further including: connecting a first source of the first concentrated medicament to the disposable component with a connector; and connecting a second source of the second concentrated medicament to the disposable component with a second connector.

According to a thirty-seventh further embodiment, there is provided the method of the thirty-sixth further embodiment or any of the other foregoing embodiments, further including: conveying the first concentrated medicament from the first source to a first concentrate container pre-attached as an empty bag to the disposable component; and conveying the first concentrated medicament from the first concentrate container to the mixing container.

According to a thirty-eighth further embodiment, there is provided the method of the thirty-seventh further embodiment or any of the other foregoing embodiments, wherein the first source is a reusable container having a greater storage capacity than the first concentrate container.

According to a thirty-ninth further embodiment, there is provided the method of the thirty-sixth further embodiment or any of the other foregoing embodiments, further including: conveying the second concentrated medicament from the second source to a second concentrate container pre-attached as an empty bag to the disposable component; and conveying the second concentrated medicament from the second concentrate container to the mixing container.

According to a fortieth further embodiment, there is provided the method of the thirty-ninth further embodiment or any of the other foregoing embodiments, wherein the second source is a reusable container having a greater storage capacity than the second concentrate container.

According to a forty-first further embodiment, there is provided the method of the thirty-fifth further embodiment or any of the other foregoing embodiments, wherein the determining of the concentration of the contents of the mixing container includes measuring a conductivity of the contents.

According to a forty-second further embodiment, there is provided the method of the thirty-fifth further embodiment or any of the other foregoing embodiments, further including: conveying a variable quantity of the purified water to the mixing container after the first mixing, wherein the variable quantity is determined based on the determined concentration of the contents.

According to a forty-third further embodiment, there is provided the method of the forty-second further embodiment or any of the other foregoing embodiments, further including: further determining a concentration of the contents at a time after the conveying of the variable quantity of the purified water to the mixing container and before the conveying of the third quantity of the second concentrated medicament to the mixing container.

According to a forty-fourth further embodiment, there is provided the method of the forty-second further embodiment or any of the other foregoing embodiments, wherein the variable quantity of the purified water is less than a difference between the first quantity of the purified water and an estimated total quantity of the purified water required in the custom mini batch of dialysate.

According to a forty-fifth further embodiment, there is provided the method of the thirty-fifth further embodiment or any of the other foregoing embodiments, further including: conveying a second variable quantity of the purified water to the mixing container after the second mixing, wherein the second variable quantity is determined based on the determined concentration of the contents of the mixing container after the second mixing.

According to a forty-sixth further embodiment, there is provided the method of the thirty-fifth further embodiment or any of the other foregoing embodiments, wherein the providing of the contents of the mixing container to the medicament user takes place less than an hour after an initiation of production of the custom mini batch of dialysate.

According to a forty-seventh further embodiment, there is provided the method of the thirty-sixth further embodiment or any of the other foregoing embodiments, further including: conveying the first concentrated medicament and/or the second concentrated medicament from the first source or the second source into a drain line to inhibit growth of pathogens in the drain line.

According to a forty-eighth further embodiment, there is provided the method of the thirty-fifth further embodiment or any of the other foregoing embodiments, wherein the conveying of the third quantity of the second concentrated medicament to the mixing container comprises conveying the third quantity of the second concentrated medicament to the mixing container in response to the determining of the concentration of the contents indicating that there is no gross error in a measurement of the concentration of the contents.

According to a forty-ninth further embodiment, there is provided the method of the thirty-fifth further embodiment or any of the other foregoing embodiments, wherein the first concentrated medicament is an osmotic agent concentrate and the second concentrated medicament is an electrolyte concentrate.

It is, thus, apparent that there is provided, in accordance with the present disclosure, Medicament Preparation Devices, Methods, and Systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A system for preparing a medicament for use by a medicament user, comprising:

a proportioning machine having a controller, a pumping actuator, and clamping actuators configured to engage a fluid circuit, the fluid circuit having a pumping portion that engages with the pumping actuator and clamping portions that engage with respective ones of the clamping actuators of the proportioning machine;

the fluid circuit having an empty mixing container attached to the fluid circuit, a first pre-attached concentrate container, and a second pre-attached concentrate container;

a first detachable container having a first concentrated medicament therein;

a second detachable container having a second concentrated medicament therein;

the proportioning machine being configured to flow a fluid from the mixing container into and out of the mixing container to circulate the fluid;

the proportioning machine being configured to flow water and the first and second concentrated medicaments into said mixing container to dilute the first and second concentrated medicaments to make a ready-to-use medicament;

the controller being configured to regulate a clamp on a return line leading to said mixing container to generate a predefined pressure in an outlet line of the fluid circuit which is attachable to an external user of the ready-to-use medicament; and the predefined pressure being maintained in the outlet line by pressure feedback control, wherein the controller is configured to control the pumping actuator and the clamping actuators to convey at least one of the first concentrated medicament from the first detachable container and the second concentrated medicament from the second detachable container into a drain line, and to hold the at least one of the first concentrated medicament and the second concentrated medicament in the drain line to inhibit bacterial growth in the drain line.

2. The system of claim 1, wherein the controller is further configured to control the pumping actuator and the clamping actuators to convey the first concentrated medicament from the first detachable container through a sterilizing filter into the first pre-attached concentrate container.

3. The system of claim 2, wherein the pumping actuator and the clamping actuators include a peristaltic pump, and the peristaltic pump operates in a first direction when the peristaltic pump conveys the first concentrated medicament into the first pre-attached concentrate container.

4. The system of claim 3, wherein the controller is further configured to control the peristaltic pump to operate in a second direction, opposite to the first direction, when first concentrated medicament is conveyed into the mixing container.

5. The system of claim 4, wherein the first concentrated medicament is conveyed from the first pre-attached concentrate container into the mixing container.

6. The system of claim 1, wherein the controller is further configured to control the pumping actuator and the clamping actuators to convey the second concentrated medicament from the second detachable container through a sterilizing filter into the second pre-attached concentrate container.

7. The system of claim 6, wherein the pumping actuator includes a peristaltic pump, and the peristaltic pump operates in a first direction when the peristaltic pump conveys the second concentrated medicament into the second pre-attached concentrate container.

8. The system of claim 7, wherein the controller is further configured to control the peristaltic pump to operate in a second direction, opposite to the first direction, when second concentrated medicament is conveyed into the mixing container.

9. The system of claim 8, wherein the second concentrated medicament is conveyed from the second pre-attached concentrate container into the mixing container.

10. A system for preparing a medicament for use by a medicament user, comprising: a proportioning machine having a controller, a pumping actuator, and clamping actuators configured to engage a fluid circuit, the fluid circuit having a pumping portion that engages with the pumping actuator and clamping portions that engage with respective ones of the clamping actuators of the proportioning machine;

the fluid circuit having an empty mixing container attached to the fluid circuit, a first pre-attached concentrate container, and a second pre-attached concentrate container;

a first detachable container having a first concentrated medicament therein;

a second detachable container having a second concentrated medicament therein;

the proportioning machine being configured to flow a fluid from the mixing container into and out of the mixing container to circulate the fluid;

the proportioning machine being configured to flow water and the first and second concentrated medicaments into said mixing container to dilute the first and second concentrated medicaments to make a ready-to-use medicament;

the controller being configured to regulate a clamp on a return line leading to said mixing container to generate a predefined pressure in an outlet line of the fluid circuit which is attachable to an external user of the ready-to-use medicament; and the predefined pressure being maintained in the outlet line by pressure feedback control, wherein the controller is further configured to control the clamping portions, the pumping actuator, and the clamping actuators to convey the first concentrated medicament from the first detachable container through a sterilizing filter into the first pre-attached concentrate container, wherein the pumping actuator includes a peristaltic pump, and the peristaltic pump operates in a first direction when the peristaltic pump conveys the first concentrated medicament into the first pre-attached concentrate container, the controller is further configured to control the peristaltic pump to operate in a second direction, opposite to the first direction, when the first concentrated medicament is conveyed into the mixing container, the first concentrated medicament is conveyed from the first pre-attached concentrate container into the mixing container, and the peristaltic pump operates in the second direction when water is conveyed into the mixing container.

11. The system of claim 9, wherein the peristaltic pump operates in the second direction when water is conveyed into the mixing container.

12. The system of claim 1, wherein the first and second concentrated medicaments and the ready-to-use medicament are for peritoneal dialysis fluid.

13. The system of claim 1, wherein the external user of the ready-to-use medicament is a peritoneal dialysis cycler.

14. The system of claim 1, wherein the mixing container is removably connected to the fluid circuit by connectors.

15. A system for preparing a medicament for use by a medicament user, comprising:

a proportioning machine having a controller, a pumping actuator, and clamping actuators configured to engage a fluid circuit, the fluid circuit having a pumping portion that engages with the pumping actuator and clamping portions that engage with respective ones of the clamping actuators of the proportioning machine;

the fluid circuit having an empty mixing container attached to the fluid circuit, a first pre-attached concentrate container, and a second pre-attached concentrate container;

a first detachable container having a first concentrated medicament therein;

a second detachable container having a second concentrated medicament therein;

the proportioning machine being configured to flow a fluid from the mixing container into and out of the mixing container to circulate the fluid;

the proportioning machine being configured to flow water and the first and second concentrated medicaments into said mixing container to dilute the first and second concentrated medicaments to make a ready-to-use medicament;

the controller being configured to regulate a clamp on a return line leading to said mixing container to generate a predefined pressure in an outlet line of the fluid circuit which is attachable to an external user of the ready-to-use medicament; and the predefined pressure being maintained in the outlet line by pressure feedback control, wherein the controller is further configured to control the pumping actuator and the clamping actuators to convey the second concentrated medicament from the second detachable container through a sterilizing filter into the second pre-attached concentrate container, the pumping actuator includes a peristaltic pump, and the controller is configured to control the peristaltic pump to operate in a first direction when the peristaltic pump conveys the second concentrated medicament into the second pre-attached concentrate container, and the controller is further configured to control the peristaltic pump to operate in a second direction, opposite to the first direction, when the second concentrated medicament is conveyed from the second pre-attached concentrate container into the mixing container.

\* \* \* \* \*